United States Patent [19]
Haber et al.

[11] Patent Number: 5,271,527
[45] Date of Patent: * Dec. 21, 1993

[54] REUSABLE PHARMACEUTICAL DISPENSER WITH FULL STROKE INDICATOR

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[*] Notice: The portion of the term of this patent subsequent to Oct. 19, 2010 has been disclaimed.

[21] Appl. No.: 931,777

[22] Filed: Aug. 18, 1992

Related U.S. Application Data

[63] Continuation-in-part of Ser. No. 924,620, Aug. 3, 1992, and a continuation-in-part of Ser. No. 862,090, Apr. 2, 1992.

[51] Int. Cl.$^5$ ............................ B67D 5/22; B67D 5/52
[52] U.S. Cl. ......................................... 222/43; 222/47; 222/137; 222/309; 222/145; 604/186; 604/191
[58] Field of Search ........................ 222/25, 26, 28, 39, 222/41, 43, 46, 47, 48, 49, 23, 14, 52, 135, 137, 145, 309, 390, 391, 386; 604/82, 186, 191

[56] References Cited

U.S. PATENT DOCUMENTS

| | | |
|---|---|---|
| 3,162,217 | 12/1964 | Poli, Jr. et al. . |
| 3,248,950 | 5/1966 | Pursell et al. . |
| 3,283,727 | 11/1966 | Rodrigues, Jr. . |
| 3,343,539 | 9/1967 | Moorhouse . |
| 3,767,085 | 10/1973 | Cannon et al. ................ 222/137 X |
| 3,831,602 | 8/1974 | Broadwin . |
| 4,040,420 | 8/1977 | Speer . |
| 4,044,757 | 8/1977 | McWhorter et al. . |
| 4,086,062 | 4/1978 | Hach ................................. 222/46 X |
| 4,273,257 | 6/1981 | Smith et al. . |

(List continued on next page.)

FOREIGN PATENT DOCUMENTS

| | | |
|---|---|---|
| 313519 | 4/1989 | European Pat. Off. . |
| 137660 | 10/1901 | Fed. Rep. of Germany . |
| 984352 | 7/1951 | France . |
| 1051010 | 1/1954 | France . |
| 1054173 | 2/1954 | France . |
| 245816 | 5/1987 | German Democratic Rep. . |
| 733168 | 7/1955 | United Kingdom . |

OTHER PUBLICATIONS

Brochure, "How to Use Your NovolinPen TM," Sep., 1990, Novo Nordisk A/S.
Brochure, "Product Information for the Novo Pen Insulin Delivery System," issue 1988, Squibb–Novo, Inc.
Brochure, "Product Information for the Novolin-Pen TM, Insulin Delivery System," issue 1988, Squibb–Novo, Inc.

*Primary Examiner*—Kevin P. Shaver
*Attorney, Agent, or Firm*—Townsend and Townsend Khourie and Crew

[57] ABSTRACT

A pharmaceutical dispenser includes a housing (4), containing two pharmaceutical cartridges (32,34), slidably mounted to a sliding body (100). A replaceable needle manifold assembly (10) is mounted to the housing and fluidly couples the cartridges with a hypodermic needle at a common exit. The sliding body is part of a reciprocating drive assembly used to drive a pair of drive stems (88) against the pistons (96, 98) of the cartridges, thus forcing predetermined amounts of the pharmaceuticals out the needle. The movement of the sliding body between retracted and post-injection positions remains constant. However, the amounts and proportions of the pharmaceuticals injected during the delivery stroke is chosen by the user using stroke adjusters (182) carried by the sliding body. A bistable status flag (186) is mounted to the sliding body to indicate when the sliding body is in the post-injection and the retracted positions. The dosage adjustments are made when the sliding body is in the post-injection position. If a dose selected is more than is available, the sliding body is prevented from moving to the retracted position so that the status flag is not tripped.

43 Claims, 15 Drawing Sheets

U.S. PATENT DOCUMENTS

| | | |
|---|---|---|
| 4,381,778 | 5/1983 | Kozam et al. . |
| 4,467,942 | 8/1984 | Oshikubo .......................... 222/47 X |
| 4,610,666 | 9/1986 | Pizzino . |
| 4,631,055 | 12/1986 | Redl et al. . |
| 4,666,430 | 5/1987 | Brown et al. . |
| 4,801,434 | 1/1989 | Kido et al. . |
| 4,846,405 | 7/1989 | Zimmermann . |
| 4,874,368 | 10/1989 | Miller et al. . |
| 4,883,472 | 11/1989 | Michel . |
| 4,962,868 | 10/1990 | Borchard . |
| 4,978,336 | 12/1990 | Capozzi et al. . |
| 5,019,048 | 5/1991 | Margolin . |

REUSABLE PHARMACEUTICAL DISPENSER WITH FULL STROKE INDICATOR

CROSS REFERENCE TO RELATED APPLICATIONS

This is a continuation-in-part of (a) U.S. patent application Ser. No. 07/924,620 filed Aug. 3, 1992 entitled "Variable Proportion Dispenser With Cartridge Replacement Assembly", and (b) U.S. patent application Ser. No. 07/862,090 filed Apr. 2, 1992 entitled "Variable Proportion Dispenser", the disclosures of which are incorporated by reference. This application is also related to U.S. patent application Ser. No. 07/808,717 filed Dec. 17, 1991 entitled "Variable Proportion Dispenser", the disclosure of which is incorporated by reference.

BACKGROUND OF THE INVENTION

Frequently a physician will prescribe two or more medications to be taken by a patient either simultaneously or as close to simultaneously as practical. This is often the case in prescribing insulin. Two basic types of insulin are most frequently prescribed: regular, a fast-acting variety, and NPH, an intermediate-acting variety. Additionally, a longer-acting type of insulin called ultralente is also available. These types of insulin differ in their onset and duration of action. Regular insulin typically has the quickest onset and the briefest duration of action. The onset and duration of insulin may be modified by chemical manipulations which include precipitation with protamine or suspension with isophane or zinc. Injectable insulin is derived from pigs and cattle, and a semi-synthetic genetically-engineered human form is available commercially.

Regardless of the final chemical composition or origin of the insulin prescribed, the physician frequently advises the patient to mix two or more types of insulin and to inject them at least once a day. Some patients respond best to a schedule of two or three daily doses, usually in conjunction with meals. Frequently trial-and-error type of evaluation is practiced to arrive at the correct dosing and combination for the individual patient. However, after this initial adjustment period, the patient may be maintained on the same dose and proportion of insulins for many weeks or months assuming that the patient's diet, activity, and state of health remain reasonably constant or predictable. An example of a typical mixture and ratio of insulins is 70% NPH and 30% regular insulin injected just prior to a meal.

The implications of insulin therapy for the patient generally include the need for two separate sets of insulin injection syringes and needles. This is because the patient will usually draw a predetermined amount of insulin from each of two vials. A sophisticated patient may be able to use a single syringe and simply draw up the correct amount from each separate insulin vial. However, he may prefer to use two separate needles because of the danger of mixing two types of insulin by using a needle "contaminated" with one type of insulin and accidentally getting some of the first insulin into the second vial from which he draws the second insulin. If the patient is not sophisticated or not adept at drawing up insulin from a vial into a syringe, he would need two needles and two syringes. He may find that he has drawn up too much insulin and then he wishes to return the excess to the vial. If he is using a single syringe, he cannot return the excess to the vial if he is presently attempting to draw insulin from the second vial. The problem of getting the correct amount and proportion of each type of insulin prescribed is an everyday difficulty which the diabetic patient may face two or three times a day.

Besides insulin, other medications may be advantageously prescribed as a simultaneous or near-simultaneous dose. For example, pain medications of the opiate family are frequently prescribed together with antiemetics. The antiemetic drugs are often useful as potentiators of narcotic painkillers and additionally they may ameliorate some of the side effects of narcotics such as nausea and vomiting. For example, a patient who has chronic pain, such as that associated with metastatic cancer, may take 50 milligrams of meperidine (a narcotic) and 25 milligrams of hydroxyzine (an antiemetic) intramuscularly several times a day. Patients having chronic pain are often managed in a long-term care facility such as a nursing home. Alternatively, an outpatient setting is sometimes feasible if the patient or his family can administer medications.

Unfortunately, many patients requiring either chronic pain medication or insulin find that they have some difficulty with their eyesight. This may be especially true of the older age group. Additionally, diabetics who require insulin replacement frequently suffer deterioration of vision as a consequence of the diabetic process. Thus, people who are often in greatest need of multiple injected medications of a defined dose and proportion may ironically find their drug regimen most difficult to regulate precisely. Another problem arises in the context of long-term care facilities such as nursing homes. Frequently the nurse who administers injectable drugs is pressed for time on medication rounds. The time pressure is compounded if the care facility is constrained by budgetary or other non-medical concerns. A device which permits accurate dosing and proportion of two or more medications and which allows for repetitive dosing in the same proportions could be useful to a variety of patients in a variety of circumstances.

SUMMARY OF THE INVENTION

The present invention is directed to a reusable pharmaceutical dispenser which provides the user with a distinct visual indication when the assembly is at the very end of its delivery (or injection) stroke and at the very end of its retraction (post-return) stroke. The invention is especially useful for dispensing different types of insulin in amounts and proportions selected by the user. Once the combined dosage is selected, both in amount and proportion, the same dosage will be automatically dispensed during each actuation cycle of the dispenser. The invention, as an insulin delivery system, permits the total amount of the insulin injected and the proportion of, for example, NPH and regular human insulin to be user selected. The dispenser is designed to permit the user to easily and quickly replace spent pharmaceuticals containing cartridges and the used manifold assembly to which the used needle is mounted.

The pharmaceutical dispenser includes a housing which contains two pharmaceutical cartridges. The housing is slidably mounted to a sliding body, preferably using a guide sleeve which acts as a an extension of the housing and slidably mounts over the sliding body. A manifold assembly is mounted to the housing and fluidly couples the interiors of the cartridges with a common exit, preferably adapted to accept a hypodermic needle for giving injections. The manifold assembly is easily removable from the housing to aid removal and replacement of spent cartridges, the used manifold assembly and the used needle without the need for special tools.

The sliding body is part of a reciprocating drive assembly used to drive a pair of drive stems against the pistons of the cartridges. Doing so forces predetermined amounts of the pharmaceuticals within the cartridges from the cartridges, to the manifold and out the common exit, typically through a hollow hypodermic needle. The sliding body can move in a proximal direction to a first, retracted (post-return) position and in a distal direction to a second, post-delivery or post-injection position, and back again, during each cycle of the dispenser.

The distance that the slider body moves relative to the housing between the first and second positions remains constant. However, the amount of liquid pharmaceutical injected during the delivery stroke is chosen by the user. This is accomplished using stroke adjusters carried by the sliding body. The stroke adjusters preferably use a threaded connection to adjust the amount of pharmaceutical to be injected from each cartridge. The position or setting of the stroke adjuster determines how far a one-way drive device (or ratchet assembly) drives the drive stem during each delivery stroke.

The one-way drive device includes an anti-backup ratchet plate, mounted to the housing, which prevents the drive stems from moving in the proximal direction during the return stroke of the sliding body. The one-way drive device also includes a pair of ratchet disks, associated with the sliding body, which drive the drive stems towards the cartridge pistons during the delivery stroke of the sliding body.

The setting of each dose adjuster is indicated using a dose indicator which changes its axial position along the sliding body according to the dosage set. This is preferably achieved using a relatively large-pitched thread along one of the dose adjuster elements so that the movement of the dose indicator is an amplified version of the dose adjuster movement.

The invention includes a status window flag, in the preferred embodiment pivotably mounted to the sliding body, to provide a visual and/or audible indication when the sliding body has been moved to the post-injection position and to the retracted position at the very end of the delivery and return strokes, respectively. This is achieved in the preferred embodiment using a status window flag pivotally mounted within a recess formed in the sliding body. The status window flag can move between two extreme positions. In one position, the status window flag directly underlies a status window formed in the guide sleeve. In the other position, a status window flag is not visible through the status window; rather, one sees a panel, typically with an informing indicator, underlying the status window.

The status window flag is preferably moved between the two extreme positions using an S-shaped, over-center spring having one end positioned adjacent to the pivot of the flag and the other one pressing against the sliding body. The over-center spring is formed and positioned such that the flag has two stable positions corresponding to the post-injection and retracted positions of the sliding body. The flag is moved between the two positions by the engagement of trip pins extending inwardly from the guide sleeve. The trip pins are positioned to engage and trip the over-center spring at the very end of travel of the sliding body. In this way, the user receives a visual and audible indication of when the sliding body is at the end of travel during each stroke to ensure that a complete injection is given. To avoid any ambiguity, the status indicator shifts suddenly and fully at the extreme positions of the stroke, so the user is never presented with a potentially confusing partly-visible retraction indication.

The dosage adjustments in the preferred embodiment are made when the sliding body is in the post-injection position. To prevent inadvertent movement of the sliding body from the post-injection position, a post-injection latch is carried by the guide sleeve. The post-injection latches automatically engages an appropriately positioned recess in the sliding body when the sliding body is in the post-injection position. Only by depressing the post-injection latch can the user move the sliding body out of the post-injection position to the retracted position.

The invention also provides an indication to the user whether there is sufficient pharmaceutical left in the cartridge for the desired set dose. In the preferred embodiment this is achieved by forming a shallow groove along a portion of a length of each drive stem. Ratchet disk housings, which are coupled through the dose adjusters to the slider housing, have inwardly projecting elements which ride in the shallow grooves. As the stems advance, the end of the shallow grooves will limit the ratchet collar and therefore the slider housing's rearward (i.e., proximal) movement. If the available remaining pharmaceutical is less than the dose selected, the slider housing will not be able to be moved to the full retracted position and will not trip the status flag to display an indicium indicating the dispenser is configured for an injection. The user can rotate the dose knob reducing the dose to permit the status flag to trip. The user can then check the dose indicator along the side of the sliding body to determine what dose of medication is available for that last injection.

When it is desired to replace a spent cartridge, the fingers of the ratchet disks and the anti-backup ratchet plate, which normally engage the drive stems, are dilated through the use of release forks positioned coaxially with the drive stems. The release forks can move independent of the drive stems. During the normal axial movement of the drive stems the release forks do not release the ratchet disks from the stems. However, when the sliding body is in the retracted position, the dose adjusters can be threaded into the sliding body to drive the release forks against the ratchet disks to dilate the fingers of the ratchet disks and thus release the ratchet disks from the drive stems. The axial movement of the release forks also forces the ratchet disk housing, which has a pair of ratchet plate release prongs, against the ratchet plate to dilate the fingers of the ratchet plate thus releasing the drive stem from the ratchet plate as well. The unintentional threading of the dose knobs into the slider housing is prevented by requirement to shift the release switch before the dose knob thread can engage the slider housing threads. The needle manifold is then separated from the cartridge housing to expose the cartridges. The cartridges are then removed to expose the drive stems. This allows the drive stems to be forced in the proximal direction back towards their initial or as-shipped positions to accommodate full replacement cartridges.

Some users may suffer from a certain degree of confusion; the simultaneous visual display of two (or more)

dose indicators when setting the dose for each component could create problems for these users. With a two-component dispenser, it is preferred that the dose indicator for each component be visually perceptible from opposite sides of the dispenser. Thus, when a user sets the dose, by rotating the dose adjustor, only one dose indicator is visible. This helps to ensure that the user does not become confused as to the dose selected.

In the present embodiment the axial position of the drive coupling prior to the return stroke determines the dose. The visual indication of this axial movement can be magnified by the dose indicator. For example, assume that an axial movement of three millimeters by the drive stem corresponds to one unit of medication. With the present invention, the dose indicator can be driven in such a way that the dose indicator moves, for example, six millimeters for every three millimeters the drive stem is to move. This permits the units of medication markings, typically carried by the sliding body, to be spaced twice as far apart as would otherwise be possible thus greatly enhancing ease of use and accuracy.

One of the primary advantages of the invention is that it permits the user to adjust both the quantity and proportion of the two components to be delivered by the dispenser. The setting stays the same for multiple duplicate doses without the need for any additional adjustment although additional adjustment is allowed.

Other features and advantages of the invention will appear from the following description in which the preferred embodiments have been set forth in detail in conjunction with the accompanying drawings.

DESCRIPTION OF THE PREFERRED EMBODIMENT

Figure 1:
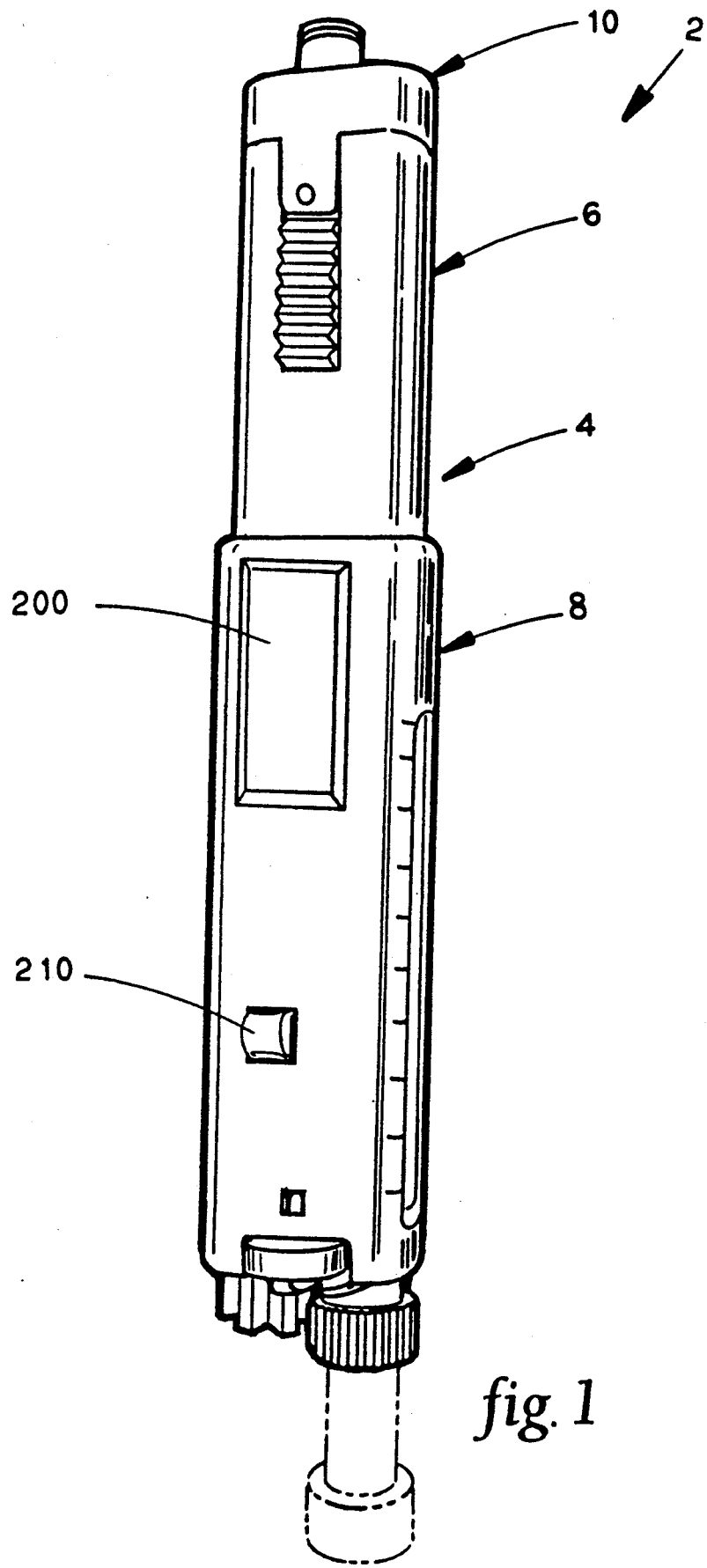
FIG. 1 is an overall isometric view of a pharmaceutical dispenser made according to the invention with the sliding body in the post-injection position.
Figure 2:
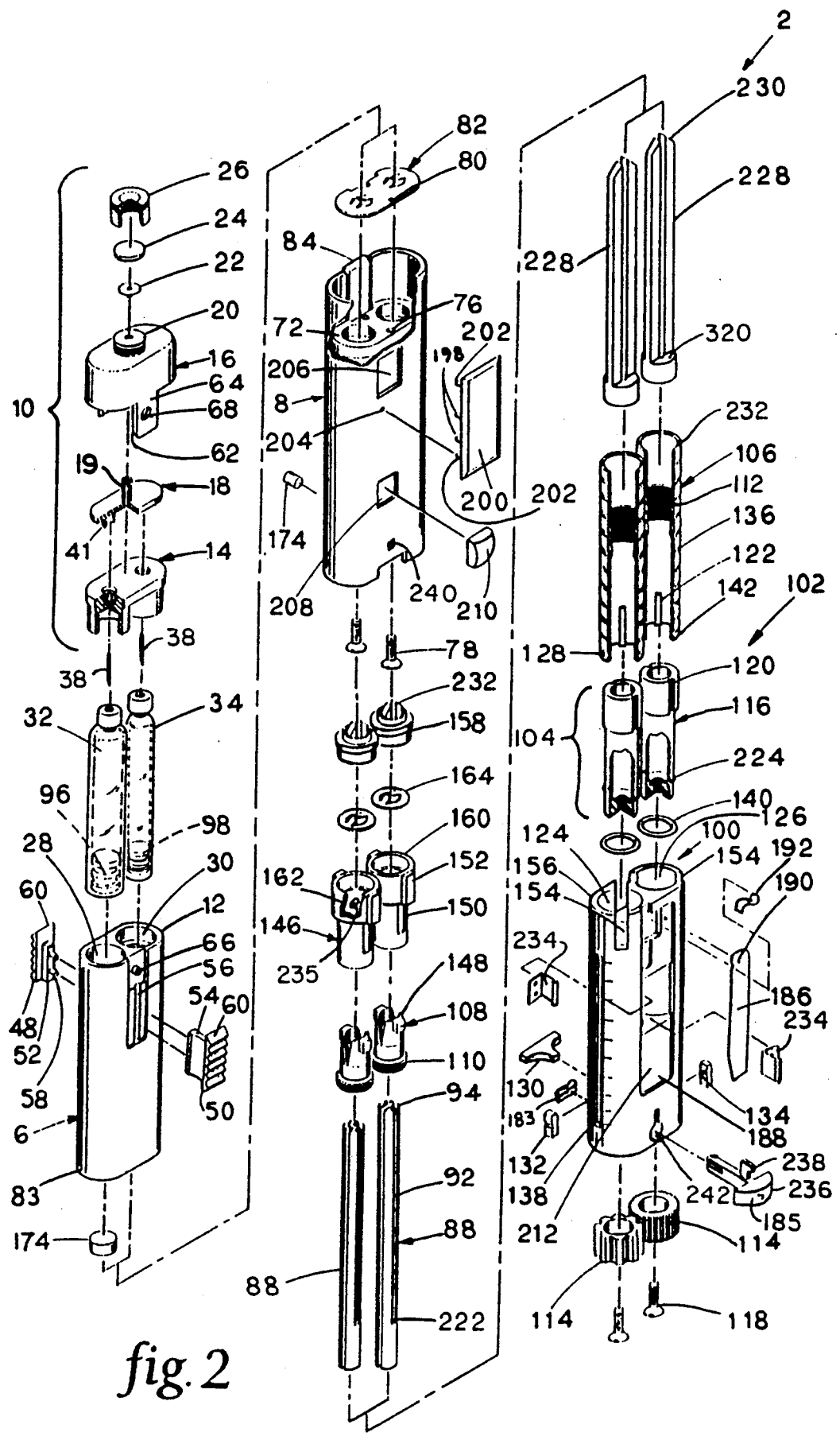
FIG. 2 is an exploded isometric view of the dispenser of FIG. 1.
Figure 3:
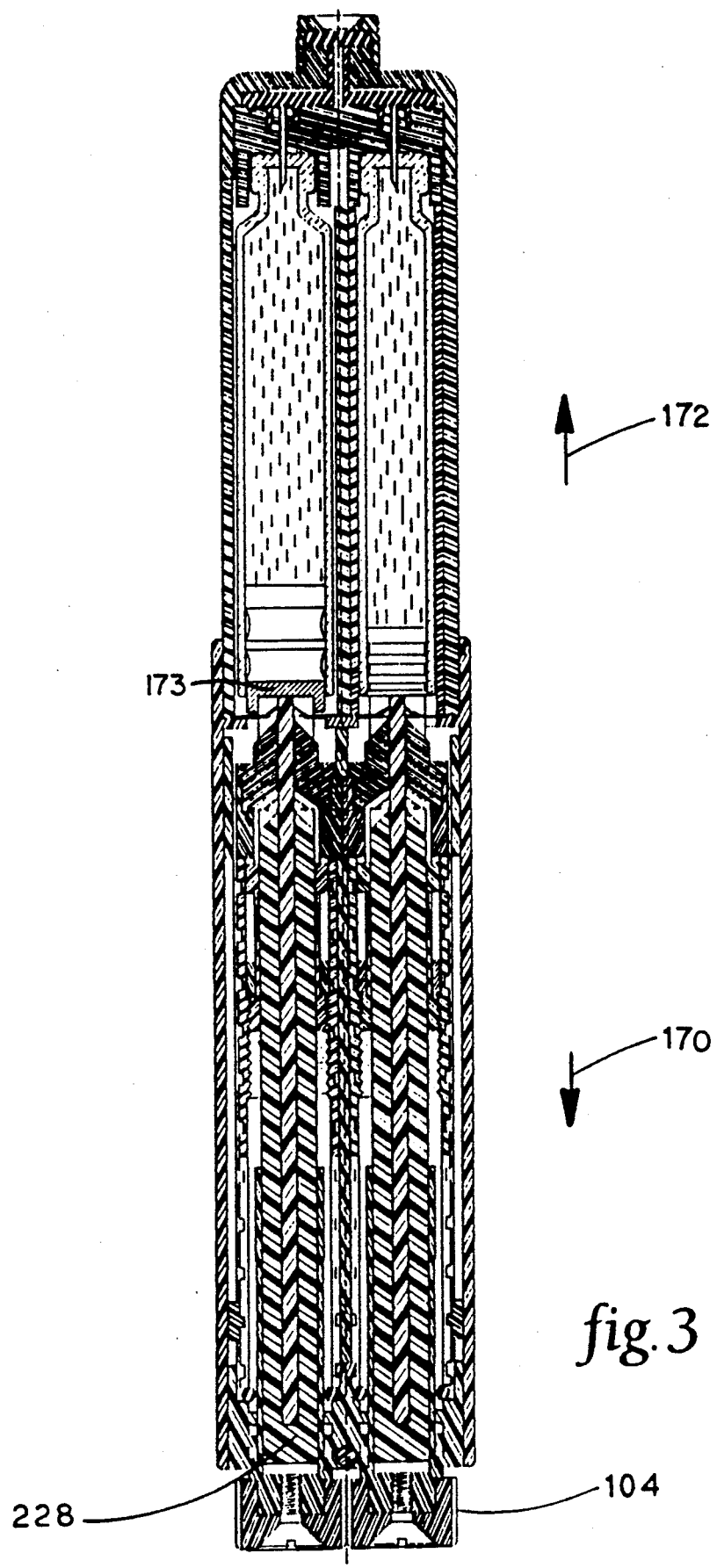
FIG. 3 is a cross-sectional view of the dispenser of FIG. 1.
Figure 4:
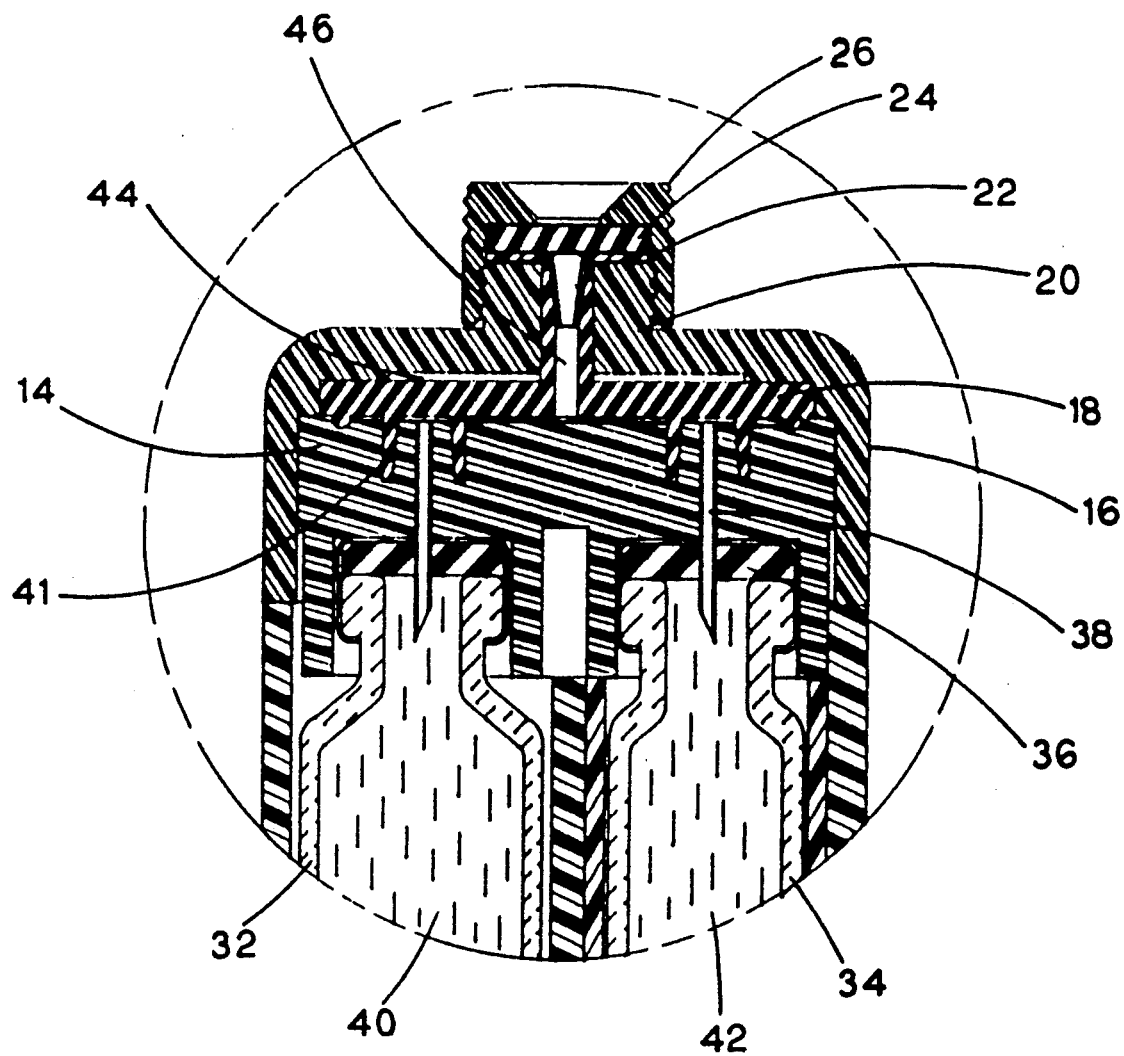
FIG. 4 is an enlarged view of the distal portion of the dispenser of FIG. 3 showing the manifold assembly.

Pharmaceutical dispenser 2 is shown in FIG. 1 to include a housing 4; housing 4 includes a cartridge housing 6 and a guide sleeve 8 secured thereto. Guide sleeve 8 acts as an extension of cartridge housing 6. Referring now also to FIGS. 2-4, a manifold assembly lo, mounted to the distal end 12 of cartridge housing 6, includes a manifold body 14, a manifold housing 16 and an elastomeric diaphragm 18 mounted between the two. The diaphragm 18 includes an upwardly extending tube 19, defining a central bore 46. Housing 16 includes a threaded tip 20 against which a needle guiding funnel 22 is mounted. Funnel 22 has a needle-pierceable septum 24 positioned against the funnel and held in place by a septum cap 26, which is threadably secured to threaded tip 20. Needle funnel 22 acts as a guide for the inner end of a double ended hypodermic needle, not shown, which is mounted to septum cap 26 when it is desired to give an injection. The funnel 22 avoids piercing the tube 19 with the inner end of the needle, and also forms a seal with the tube 19, since the outer diameter of the upper end of the funnel 22 is greater than the diameter of the bore 46, causing the upper end of the tube 19 to elastically distend and form a tight seal with the funnel 22.

Cartridge housing 6 includes a pair of cartridge receiving bores 28, 30 sized to accept cartridges 32, 34. Cartridge 32 is preferably a 3 ml cartridge while cartridge 34 is a 1.5 ml cartridge; however, other size cartridges or the same size cartridge could be used as well. Cartridges 32, 34 each have a septum 36 (FIG. 4) at one end which is pierced by a spike 38 extending from manifold body 14. Doing so permits the contents 40, 42 of cartridges 32, 34 to flow through spikes 38 and past cup-shaped extensions 41 of diaphragm 18 between relatively rigid manifold body 14 and elastomeric diaphragm 18. The necessary upward deflection of diaphragm 18 is possible due to presence of a region 44 defined between diaphragm 18 and manifold housing 16 (FIG. 4). Contents 40, 42 then continue up a central bore 46 formed in diaphragm 18 where the contents can flow into the inner end of the double ended hypodermic needle (not shown) mounted to septum cap 26. Accordingly, manifold assembly 10 provides a central or common exit for contents 40, 42. Diaphragm 18 and particularly the cup-shaped extensions thereof 41 act as a check-valve to prevent flow through the spikes 38 except under circumstances in which the contents 40, 42 of the cartridges 32, 34 are sufficiently pressurized (e.g., with respect to the pressure at the distal ends of the spikes 38) that flow through the spikes 38 is guaranteed to be outflow. This guards against cross-contamination of the cartridges and waste of pharmaceuticals, e.g., by preventing fluid exit when no needle is installed.

The natural resiliency of the diaphragm 18 aids in reducing the amount of residual pharmaceutical, i.e., the pharmaceutical which has exited the cartridges 32, 34, but is not expelled from the needle. It is desired to reduce the residual to avoid the potential for bacterial growth or other contamination. According to one embodiment, residual is reduced by expelling pharmaceutical even after flow of pharmaceutical through the spikes has ceased. This is achieved by relying on the natural resiliency of the diaphragm 18 to cause the diaphragm to relax into its preferred position adjacent the manifold body 14 thus expelling pharmaceutical which may be contained between the manifold body 14 and the diaphragm 18 through the central bore 46.

Cartridge 6 has a pair of manifold assembly release buttons 48, 50 slidably mounted to the housing. Buttons 48, 50 have extensions 52, 54 which extend into a guide slot 56 formed in cartridge housing 6. Extensions 52, 54 are secured to one another within slot 56 by the engagement of a pair of pins 58 extending from extension 52 which engage complementary holes (not shown) formed in extension 54 and secured in place through use of an adhesive or through a friction fit. Slot 56 is sized to permit buttons 48, 50 to move axially toward and away from manifold assembly 10. Leading surfaces 60 of buttons 48, 50 are shaped and positioned to engage internal bevels 62 formed on the proximal ends of a pair of tabs 64 of manifold housing 16. To remove manifold housing 10, the user forces buttons 48, 50 towards manifold assembly 10, that is in the distal direction, so that surfaces 60 engage internal bevels 62. This deflects tabs 64 outwardly so that pegs 66, extending from cartridge housing 6, are disengaged from holes 68 formed in tabs 64 to permit the user to pull a manifold assembly 10 away from cartridge housing 6. Doing so exposes cartridges 32, 34 so that they can be removed and replaced as desired.

Figure 7:
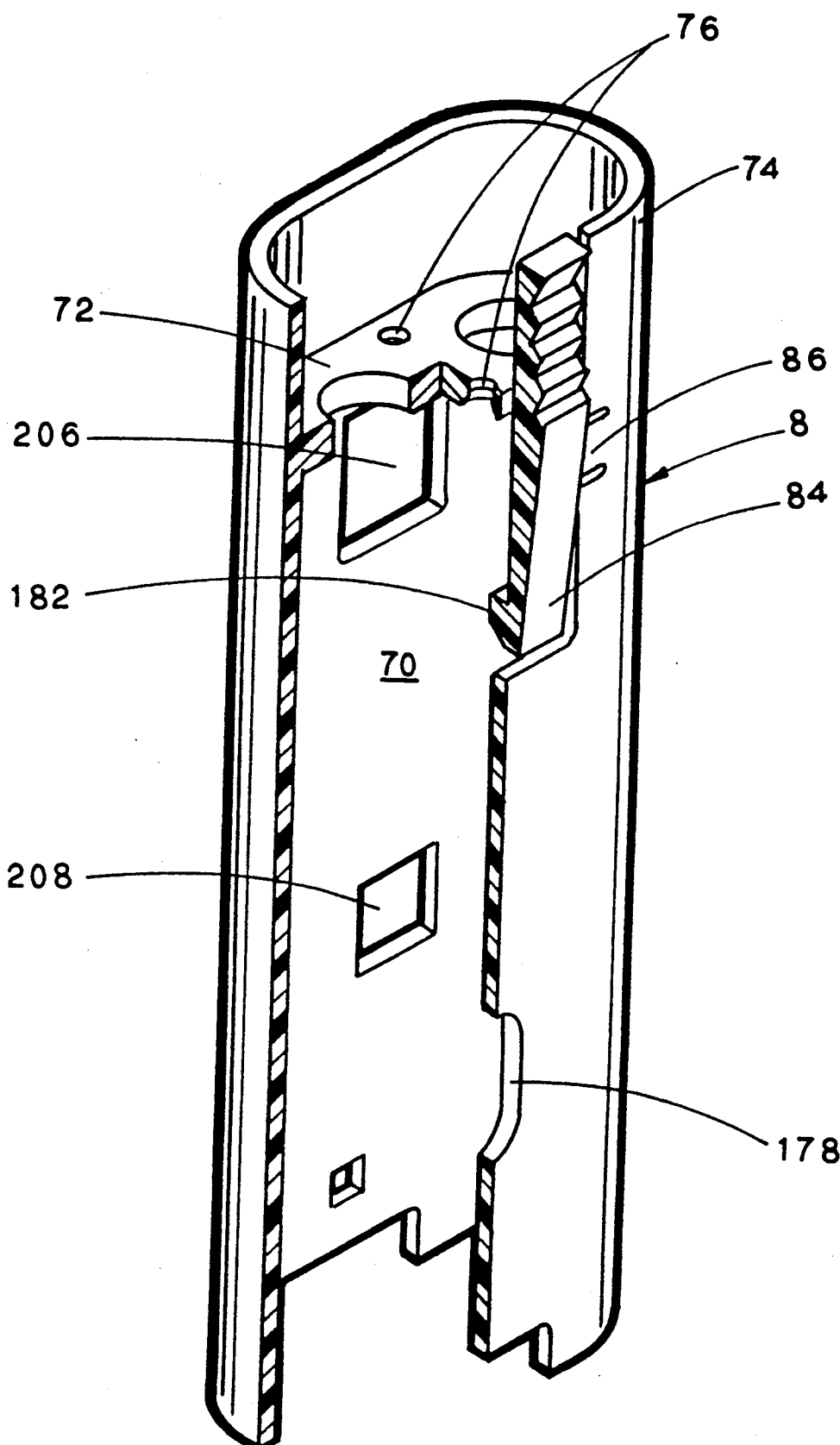
FIGS. 7 and 7A are enlarged isometric views of the guide sleeve and sliding body housing of FIG. 2 with quarter sections removed to illustrate internal detail.

Guide sleeve 8, also shown in FIG. 7, has a generally open interior 70 with a ledge 72 formed near the distal end 74 of the guide sleeve. Ledge 72 has a pair of holes 76 sized to accept screws 78 (see FIG. 2). Screws 78 pass through holes 76, through holes 80 formed in an anti-backup ratchet plate 82, discussed below, and into threaded holes, not shown, formed in the proximal end 83 of cartridge housing 6. Accordingly, cartridge housing 6 and guide sleeve 8 are rigidly secured to one another. Guide sleeve 8 includes an integrally formed post injection latch 84 connected to guide sleeve 8 through tabs 86. The use of latch 84 will be discussed below.

Figure 5:
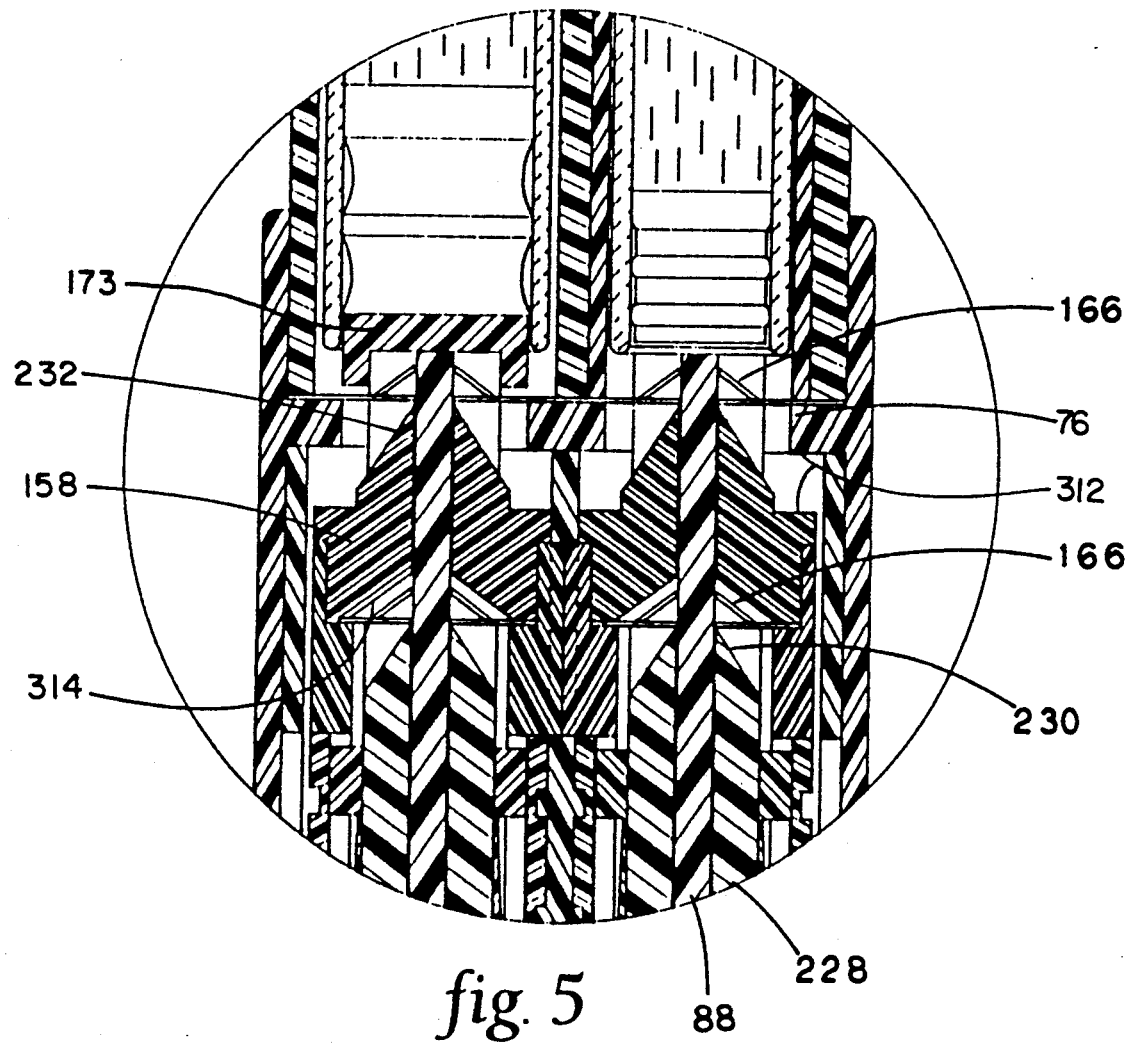
FIG. 5 is an enlarged view of the central portion of the dispenser of FIG. 3 showing the release forks and the release prongs opposite the ratchet disks and the anti-backup ratchet plate in the non-release status.
Figures 5A, 5D:
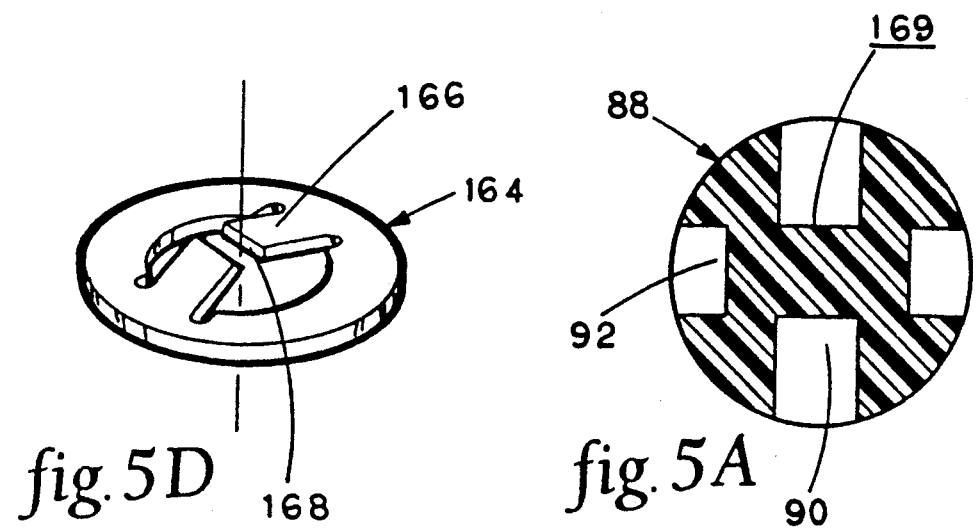
FIG. 5A is a cross-sectional view of a drive stem of FIG. 2.
FIG. 5D is an isometric view of a ratchet disk of FIG. 2.

Dispenser 2 includes a pair of drive stems 88 which have a pair of longitudinal drive grooves 90, see FIG. 5A, formed along their entire lengths and a pair of shallow end-of-dose grooves 92 formed along a portion of their lengths. The distal ends 94 of drive stems 88 are forced against the pistons 96, 98 of cartridges 32, 34 through the use of a reciprocating drive assembly.

Figure 6:
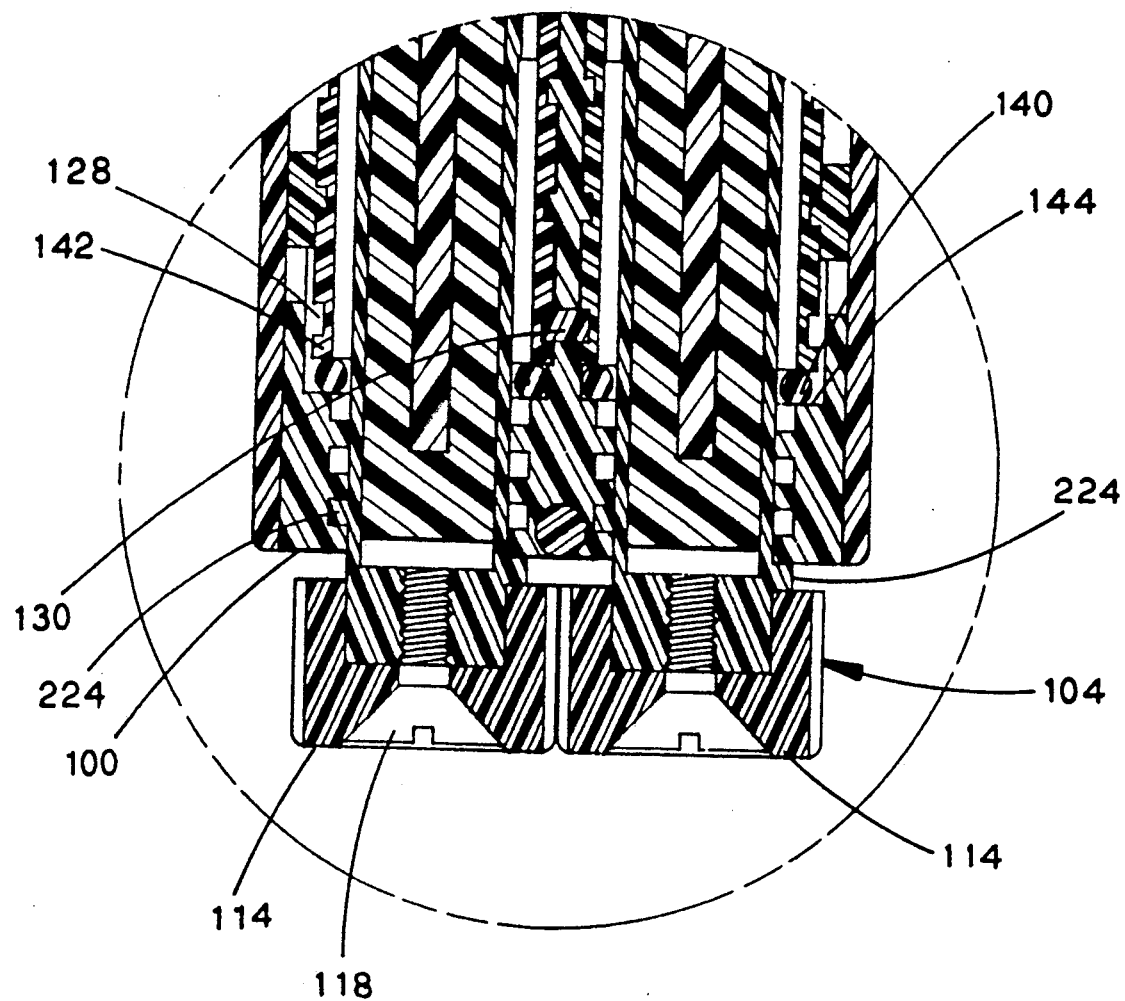
FIG. 6 is an enlarged view of the proximal portion of the dispenser of FIG. 3 illustrating the abutment of the external thread on the knob core against the proximal end of the sliding body.
Figure 7A:
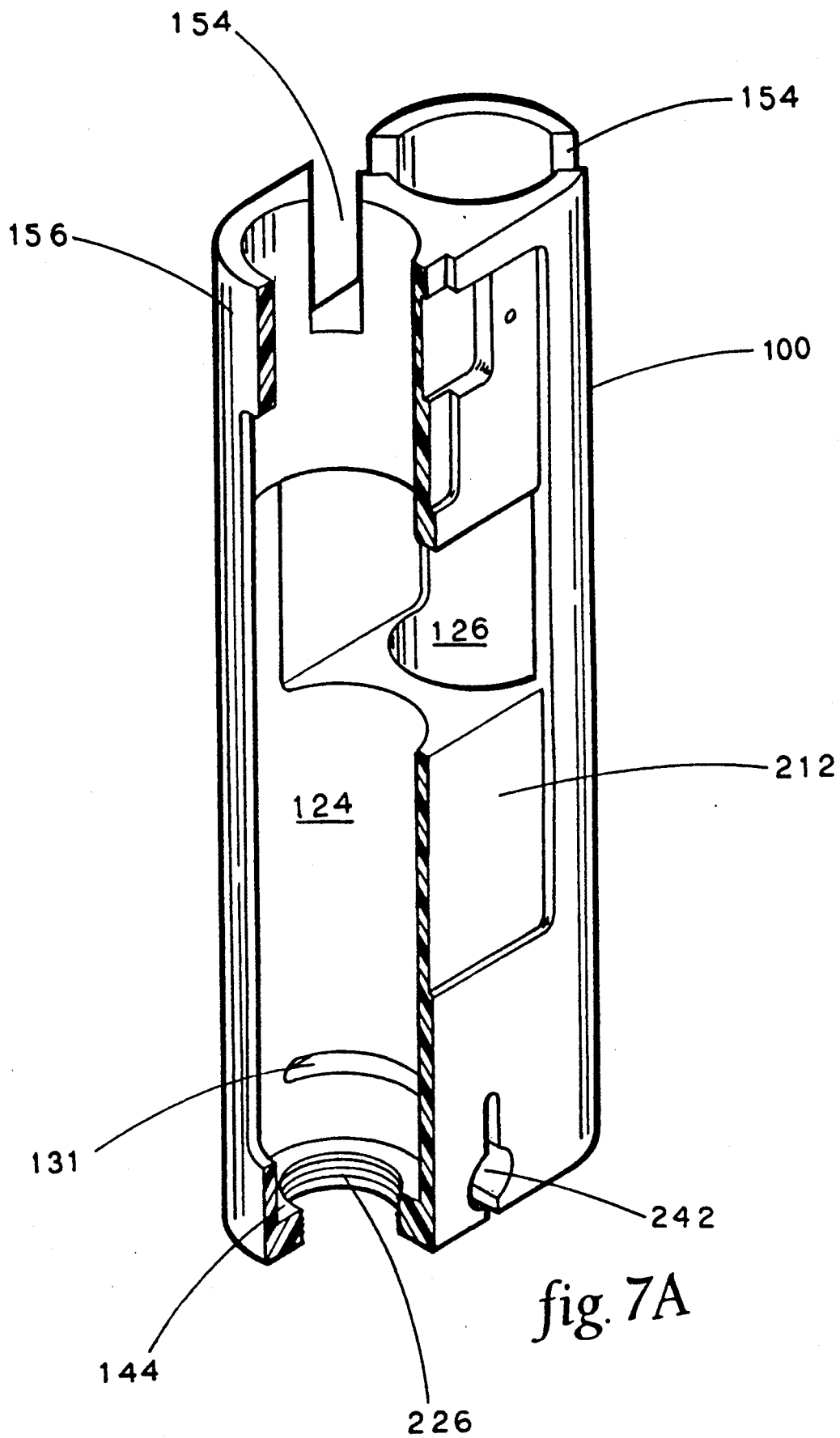

The reciprocating drive assembly includes a sliding body 100 to which is mounted a pair of dose adjusters 102 (see FIGS. 2, 3 and 7A). Dose adjusters 102 each include a dose adjustment screw driver 104 which is operably connected to a dose adjustment screw 106. A drive coupling 108 has external threads 110 which mate with internal threads 112 on screw 106. Screw drivers 104 each include a dose knob 114 mounted to a knob core 116 by a screw 118 (see FIGS. 2 and 6). Knob cores 116 are keyed to dose adjustment screws 106 through the use of grooves 120 formed on knob cores 116 and inwardly extending splines 122 formed within screws 106. This permits the user to transfer rotary motion from dose knobs 114, through knob core 116 and to dose adjustment screws 106 while permitting the dose adjustment screw drivers to be moved in a proximal direction away from sliding body 100. This aids user manipulation of dose knobs 114 as shown in FIG. 1.

Preferably, as shown in FIG. 2, the splines 122 extend only partially up the interior surface of the knob cores 116. Thus, in the normal operating position, with the knobs 114 adjacent the release switch 236 (as described more fully below) the grooves 120 will be positioned above the splines 122 so that there will be no rotational engagement of the screwdrivers 104 with the dose adjustment screws 106. This avoids inadvertent dose changes when the dispenser 2 is in its operating configuration.

When it is desired to change a dose, preferably while the dispenser 2 is in its post-injection position, the user pulls on one of the knobs 114 to retract the knob and attached knob core 116 downward partially through the dose adjustment screw 106 to the position depicted in phantom lines in FIG. 1 so as to engage the grooves 120 with the splines 122. Once one of the knobs 114 is in this position, rotating the knob 114 will cause rotation of the knob core 116 and the engagement of the grooves 120 with the splines 122 will also cause rotation of the dose adjustment screws 106. By moving one of the knobs 114 outward before adjusting a dose, it is possible to position one of the dose adjustment knobs 114 away from the other during the dose adjustment procedure, thus making it easier for the user to rotate one of the dose adjustment knobs without moving the other. Following the rotation of the withdrawn knob to achieve the desired dose adjustment, the knob is then pushed back toward the body of the dispenser 2, adjacent the release switch 236 and, if desired, the user may then adjust the dosage on the other side by retracting and rotating the second knob.

Dose adjustment screws 106 are free to rotate within bores 124, 126 of sliding body 100. Screws 106 have circumferential grooves 128 at their proximal ends. An arcuate T-shaped adjustment screw keeper 130 is mounted in a slot 131 in sliding body 100 and engages grooves 128 to maintain screws 106 in a fixed axial position within sliding body 100 while permitting rotation. The rotary movement of each of screws 106 is indicated by the movement of a dose indicator 132. Each indicator 132 has an inwardly directed follower 134 which engages a large pitched external thread 136 formed on the outside of screws 106. Dose indicators 132 ride within slots 138 formed in sliding body 100. In one embodiment, it is desired to provide for clarity of the dose indication by using a dose indicator mechanism which amplifies the movement of the screw-drive coupling engagement 116, 110. In this embodiment, amplification is provided by using a pitch for the threads 136 which is larger for the pitch for the internal threads 112 of the screw 106. For example, if the internal threads 112 have a pitch of 23 threads per inch, the external threads 136 can be with a pitch of, for example, $3\frac{1}{4}$ threads per inch to provide an amplification of about 6.5. Such amplification provides a clear visual indication of dosage, despite relatively small adjustment of a coupling body 110 engagement with the screw threads 112, which is particularly useful for users with impaired vision. Elastomeric O-rings 140 are positioned between the proximal ends 142 of dose adjustment screws 106 and an internal ledge 144 of sliding body 100. This provides sufficient frictional resistance to maintain adjustment screw driver 104 at an axial position selected by user.

In one embodiment, it is preferred to prevent over-rotation of the screws 106, and in particular to prevent rotation which will drive the coupling 108 either proximally or distally out of engagement with the threads 112. Over-driving in one direction, e.g., proximally, can be prevented by providing a positive stop in the last thread of the internal threads 112. However, it is desired to assemble the dispenser 22 by a procedure which includes threading the coupling threads 110 into engagement with the screw threads 112 and thus it is not practical in this embodiment to provide positive stops at both ends of the threads 112. Therefore, another device can be used to prevent over-driving the coupling 108 in a distal direction. It is possible to rely on contact of the dose indicator 132 with the end of one of the slots 138 as a stop to indicate the preferred end of travel of the coupling 108 with respect to the threads 112. However, if a user attempts to rotate the knobs 114 after the indicators 132 reach the end of the slots 138, by applying sufficient force, the user may drive an indicator 132 underneath the slider housing, thus over-driving the coupling 108 and eventually damaging the dispenser 2.

Figure 11:
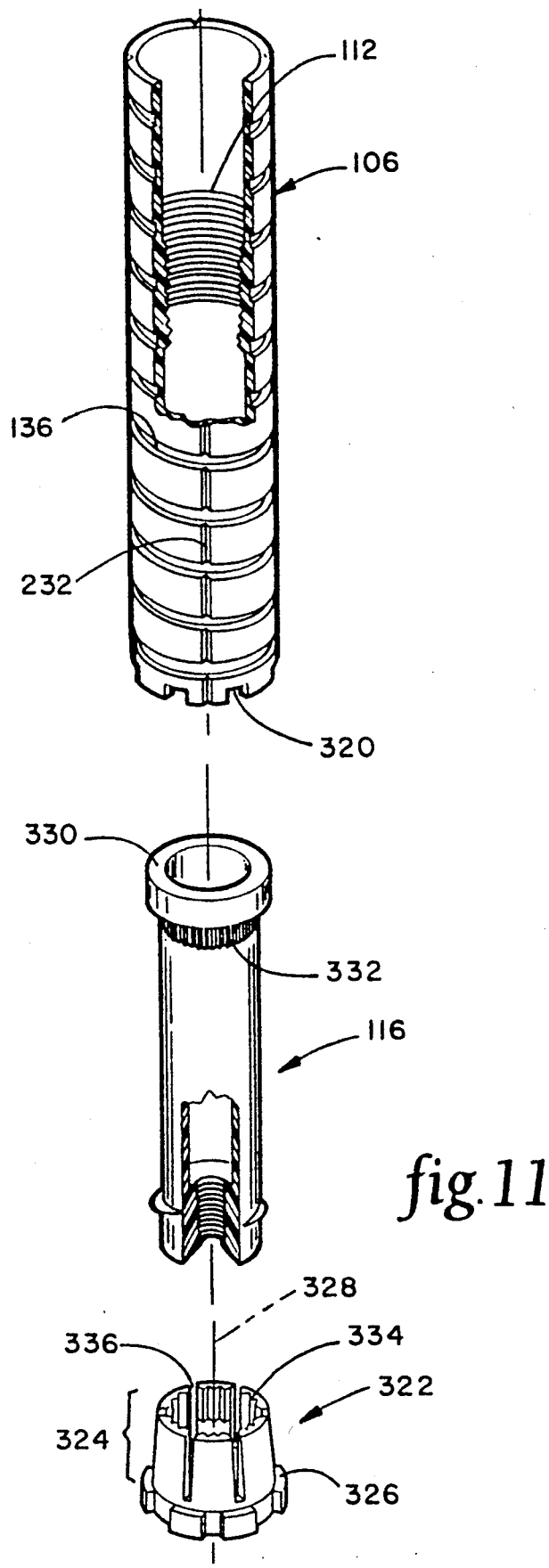
FIG. 11 is an exploded view partly cut-away of an alternative embodiment for the engagement of the knob core with the screw, using a slip clutch mechanism.

FIG. 11 depicts an alternative embodiment that can be used to prevent over-driving the coupling 108. In the embodiment of FIG. 11, the proximal rim of the screw 106 is castellated to provide a plurality of detents 320. A dilating bushing 322 has a tapered portion 324 configured to fit within the proximal interior volume of the screw 106 and having a plurality of exterior teeth 326 which inter-digitate with detents 320 so that torque about axis 328 applied to the bushing 322 will be transmitted by the teeth 326 to the screw 106 normally causing rotation thereof. The bushing 322 is held in an inter-digitating position with the screw 106, e.g., by an o-ring similar to the o-ring 140 depicted in FIG. 2. A knob core 116' is provided which is similar to the knob core 116 depicted in FIG. 2 except that the flange 330 may have a smaller axial extent than the corresponding flange of the core 116, and need not have grooves 120, and also includes external teeth 332. The external teeth 332 of the knob core 116' are configured to mesh with internal teeth 334 formed in the tapered portion 324 of the bushing 322. In order to rotate the screw 106 for dosage adjustment purposes, a knob 114 attached to the proximal end of the knob core 116' is pulled proximally to partially withdraw or "telescope" the knob core to a position similar to that depicted by phantom lines in FIG. 1. When the core 116' is withdrawn to this position, the external teeth 332 mesh with the internal teeth 334. When the knob core 116' is rotated (e.g., by rotation of an attached knob 114) about axis 328 this torque is transmitted by the teeth 332, 334 to create a torque about axis 328 on the bushing 322. The bushing on torque 322 is, in turn, transmitted by teeth 326 in detents 320 to the screw 106, normally resulting in rotation thereof about axis 328. The tapered portion 324 includes one or more slots 336 to permit the tapered portion 324 to dilate outward when subjected to a sufficiently great outward force and to return to the tapered configuration depicted in FIG. 11 by virtue of the resiliency of the tapered portion 324. When the dosage indicator 132 riding in the external threads 136 of the screw 106 reach the end of one of the slots 138, further movement of the dose indicator is resisted by the end of the slot 138 and this in turn causes resistance to continued rotation of the screw 106. This resistance to rotation of the screw 106 is sufficiently great that continued torque on the knob core 116' (e.g., by continued torque on a knob 114) causes the teeth 133 to travel up the side of the meshing teeth 334 of the bushing 322, causing dilation of the tapered portion 324. The tapered portion 324 has sufficient taper that it can dilate in amount large enough to permit the external teeth 332 to ride over the meshing teeth 334. Thus, continued attempts to rotate a knob 116 after the indicator 132 has reached the end of the slot 138 will not produce further rotation of the screw 106 but will, instead, cause the slip clutch mechanism 322, 332 to effectively disengage so that the knobs 114 will be turned without the corresponding rotation of the screw 106. During this operation, the user will receive a tactile vibrating or buzzing feedback to signal the user that the end of the dose adjustment scale has been reached. This tactile feedback is useful particularly with vision-impaired users. In addition to providing tactile feedback and avoiding over-driving of the coupling 108, the embodiment of FIG. 11 is also advantageous over the embodiment depicted in FIG. 2 because it can be more easily molded.

The rotary motion of screws 106 imparts an axial motion to drive couplings 108. This occurs because drive couplings 108 are connected to ratchet disk housings 146 through the engagement of lugs 148 within axially-extending drive slots 150 formed in generally cylindrical housings 146. Housings 146 include radially outwardly extending drive lugs 152 which are housed within slots 154 formed at the distal end 156 of sliding body 100. Accordingly, rotary movement of screw 106 causes axial movement of drive coupling 108 through the engagement of threads 110, 112 since coupling 108 and housing 146 are both prevented from rotary motion within sliding body 100 by the engagement of guide lugs 152 within slots 154.

Figure 5B:
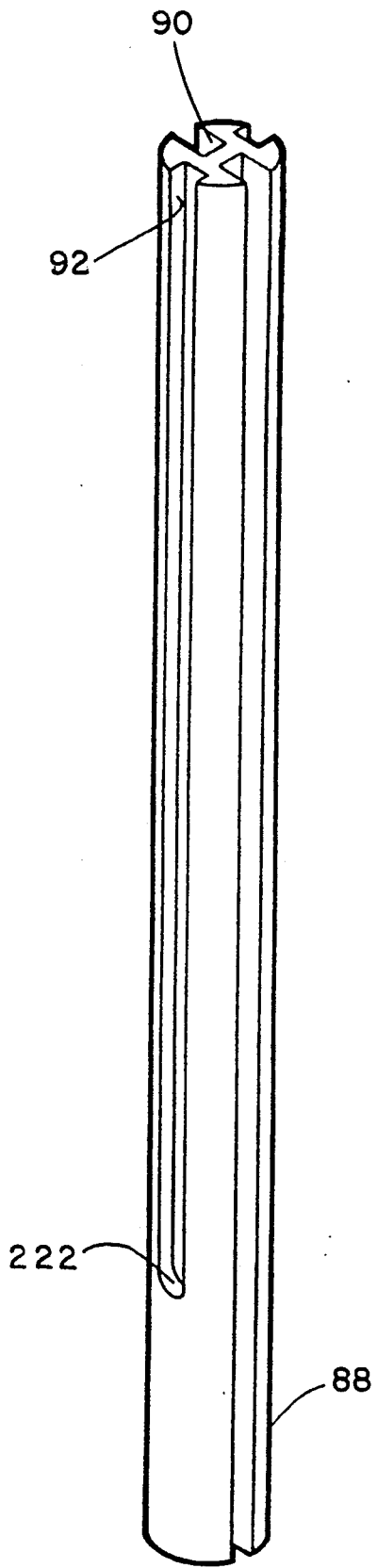
FIG. 5B is a perspective view of a stem usable in connection with a 3.0 ml cartridge.
Figure 5C:
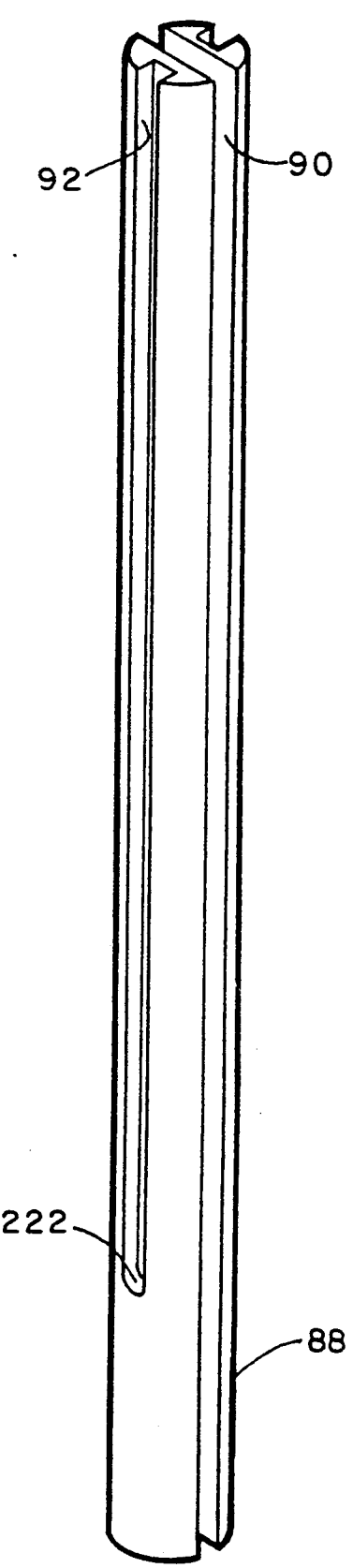
FIG. 5C is a perspective view of a stem usable in connection with a 1.5 ml cartridge.

Ratchet disk housing 146 also includes a cap 158 which is press-fit onto the distal end 160 of housing body 162 to capture a ratchet disk 164, preferably made of spring quality stainless steel, within housing 146. Ratchet disk 164 is shown in more detail in FIG. 5B and includes a pair of upwardly extending spring fingers 166 sized to fit within drive grooves 90 of drive stems 88. The tips 168 of fingers 166 are positioned to frictionally engage the drive surfaces 169 formed at the base of drive grooves 90. Accordingly, when sliding body 100 moves within guide sleeve 8, dose adjuster 102 moves with the sliding body. Depending upon the relative position of lugs 148 within slots 150, drive couplings 108 may force ratchet disk housing 146 in a distal direction, that is in the direction of arrow 172 in FIG. 3,, or in a proximal direction, that is in the direction of arrow 170. When housing 146 moves in the distal direction, ratchet disks 164 force drive stems 88 in the distal direction, thus forcing pistons 96, 98 in the distal direction causing contents 40, 42 to flow through the common exit. It should be noted that a relatively rigid, cupped shaped spaced 173 is used between drive stem 88 and piston 96. This is to accommodate the larger sized piston and minimize piston distortion.

Drive stems 88 also pass through anti-backup ratchet plate 82 which is configured similar to ratchet disks 164. Ratchet plate 82 prevents the movement of drive stems 88 in the proximal direction after having been driven by ratchet disks 164 in the distal direction. The movement of sliding body 100 in distal direction 172 is halted by the abutment of distal end 156 of sliding body 100 against ledge 72 of guide sleeve 8. The movement of sliding body 100 in proximal direction 170 is halted by the engagement of a limit pin 174 against the proximal end 176 of a retract limit slot 178. See FIGS. 9, 9A and 9B. In the preferred embodiment the total reciprocal distance of movement of sliding body 100 is about 7 mm.

Figure 9:
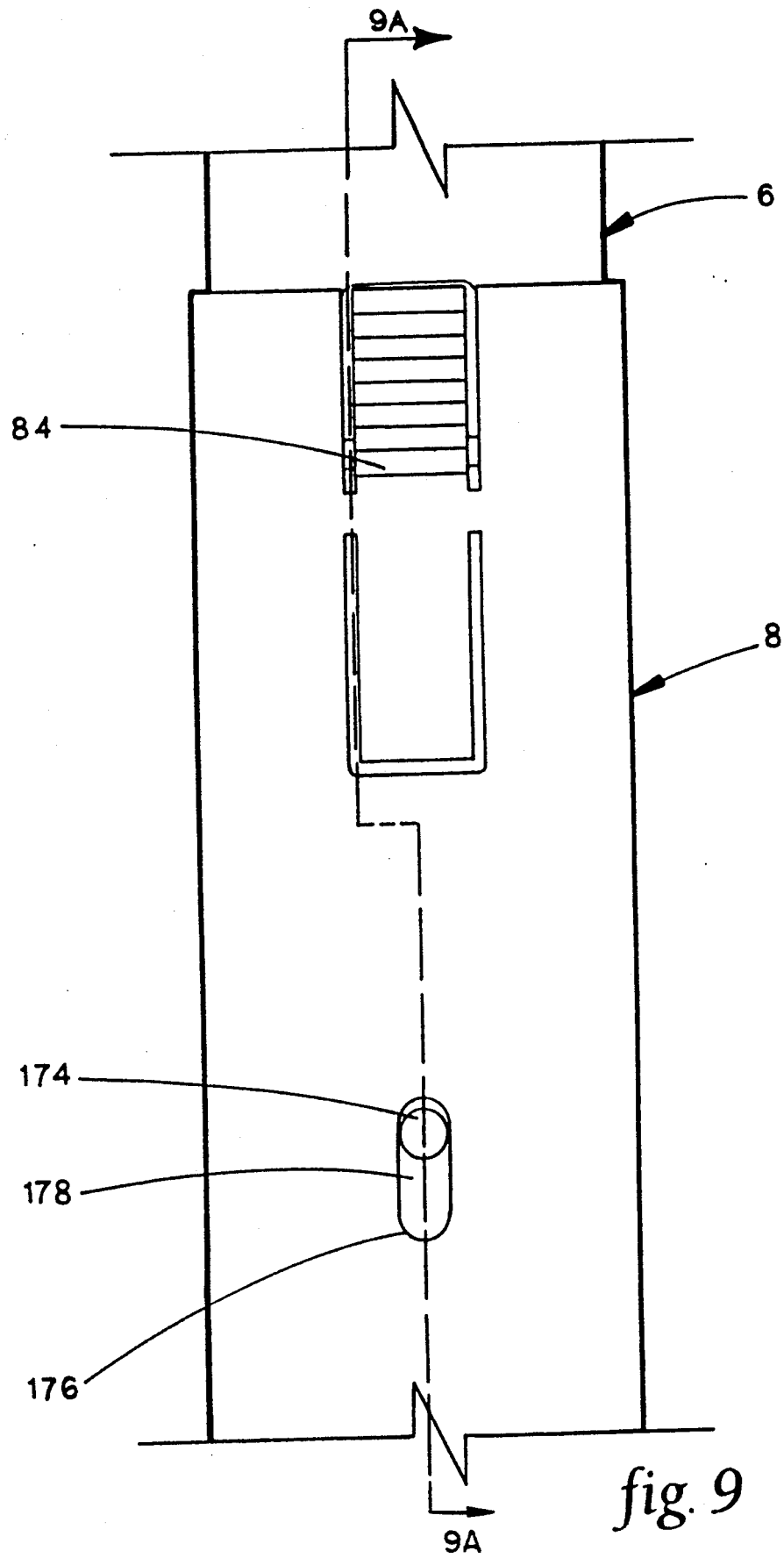
FIG. 9 is a simplified enlarged rear view of the guide sleeve of FIG. 1 showing the post-injection latch and limit pin.
Figure 9A:
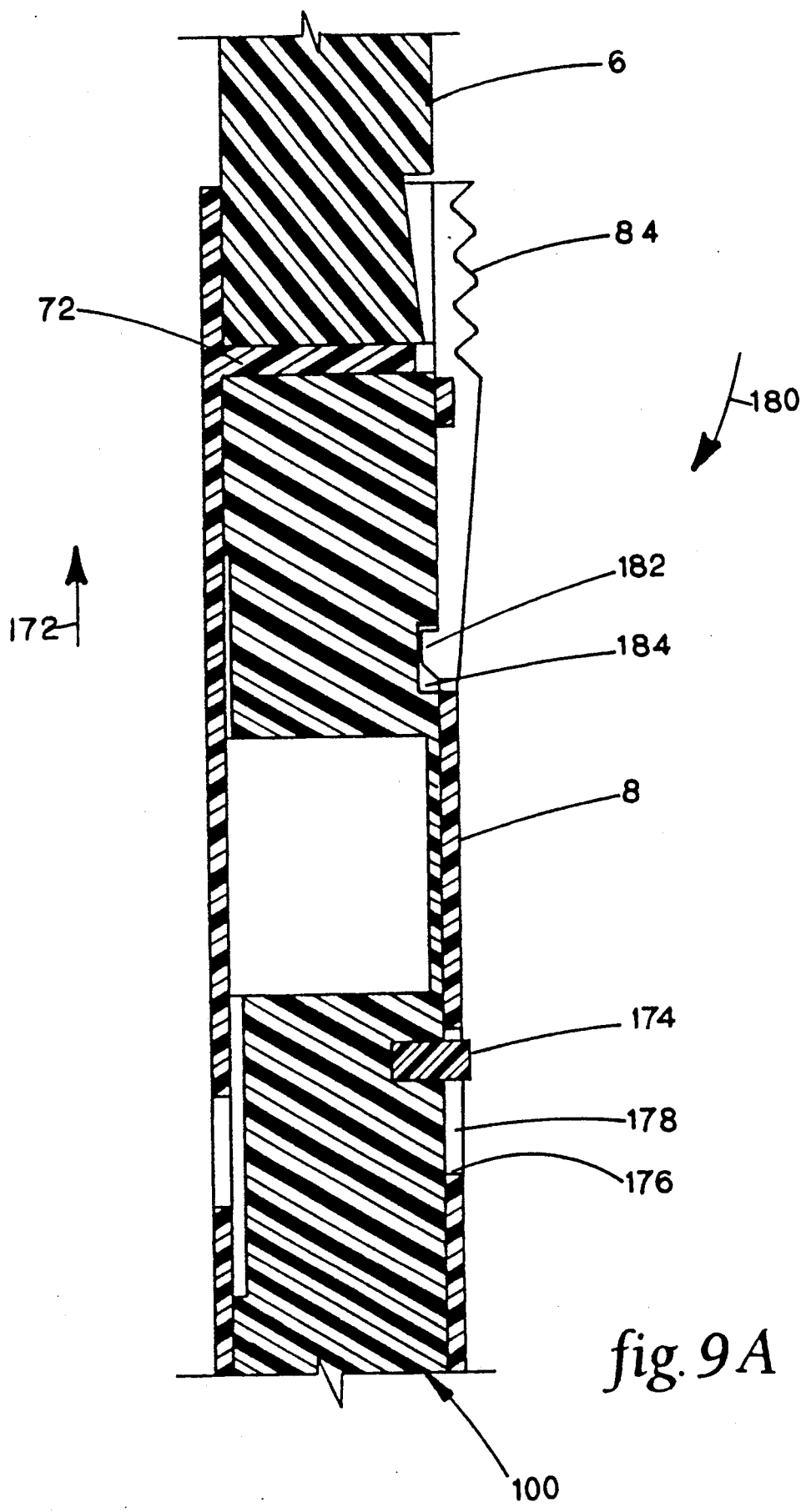
FIG. 9A is a cross-sectional view taken along line 9A—9A of FIG. 9 in the post-injection configuration with the post-injection latch engaging a recess in the sliding body and the limit pin extending from the sliding body into a retract limit slot formed in the guide sleeve.
Figure 9B:
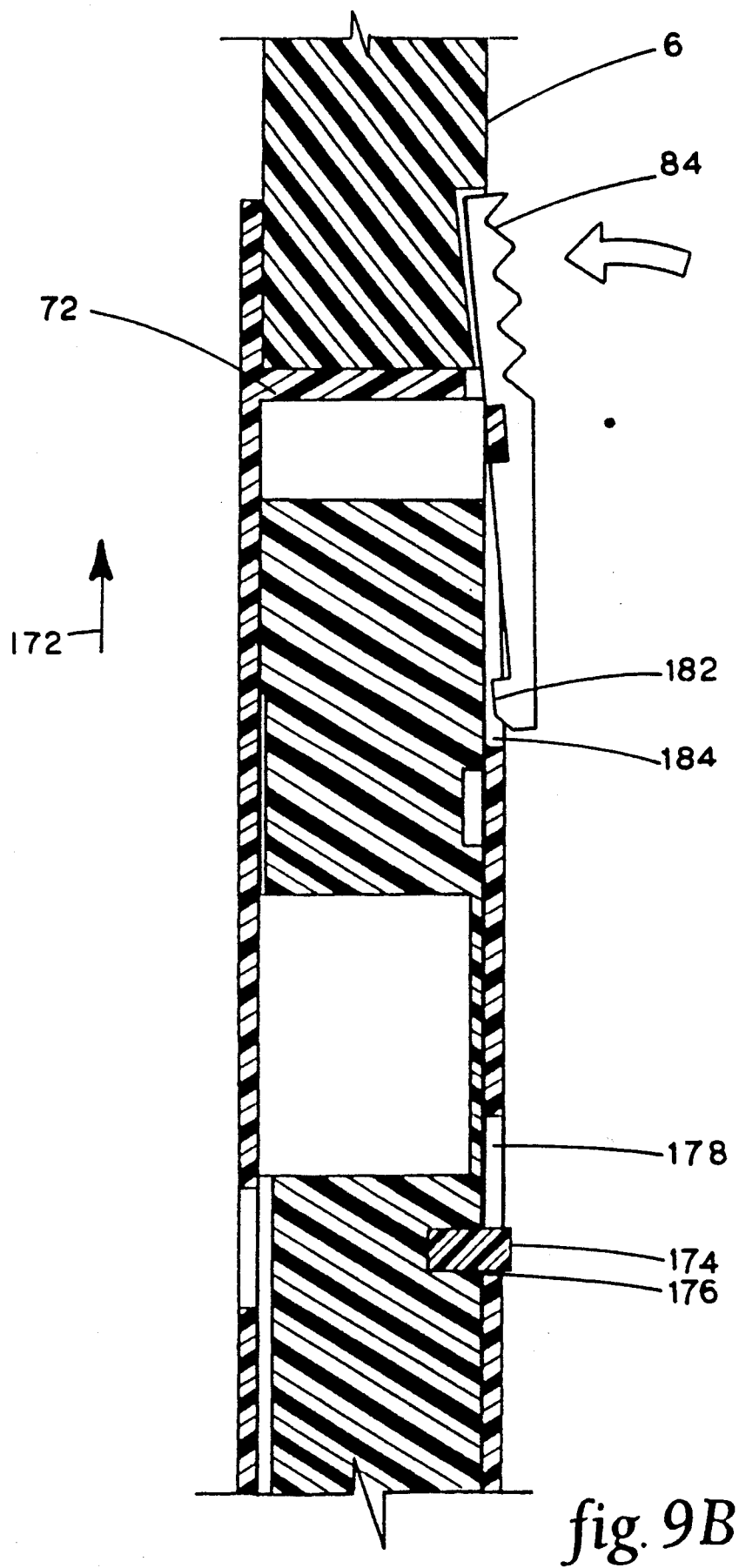
FIG. 9B is similar to FIG. 9A but shows the pivotal movement of the post-injection latch to disengage from the recess in the sliding body to permit the sliding body to be moved in a proximal direction until the limit pin contacts the distal end of the retract limit slot, typically a distance of 7 millimeters.

FIGS. 9–9B also illustrate the action of post-injection latch 84. FIG. 9A illustrates dispenser 2 after the sliding body is at the end of the delivery stroke so it is in the post-injection position. When this occurs, latch 84, which is naturally biased in the direction of arrow 180, keeps sliding body 100 in the post-injection position by the engagement of tip 182 of latch 84 into a recess 184 formed in slider body 100. The recess 184 is configured to limit the movement of the latch 84 to prevent excessive movement. This helps prevent inadvertent movement of slider body 100 from the post-injection position of FIG. 9A. When it is desired to move slider body 100 in the proximal direction 170, the user presses on latch 84 so as to pivot the latch in the direction opposite of arrow 180 against the normal bias of the latch to move tip 182 out of recess 184 as shown in FIG. 9B. The dispenser 2 is configured to facilitate the retraction of the slider body 100, by, e.g., the positioning of the post-injection latch 84 and providing retraction tabs 183, 185. Preferably, retraction tab 185 is formed as the head of the release switch 236, described more fully below. The tabs 183, 185 are positioned on the exterior surface of the sliding body 100 near the proximal edge thereof. In one preferred retraction procedure the user grasps the dispenser 2 such that, e.g., the left hand is positioned to hold down the post-injection latch 84 in its released position with the dispenser 2 in a substantially horizontal position and with the status window 208 (described more fully below) upward so as to be visible. The user than grasps the tabs 183, 185 with the right hand and pulls the slider body 100 proximally toward the retracted position until full retraction is indicated in the status window 208, as described below. By providing the described position of the post-injection latch 84 and tabs 183, 185, the user is encouraged to perform retraction in a manner which will permit the user to view the window 208 and will avoid direct compression on the slider body 100, instead, directing pressure to the tabs 183, 185.

It is useful to provide the user with reliable and unequivocal indication that the dispenser 2 has been fully retracted and is in condition for administering an injection. In the depicted embodiment, this is achieved by providing indicia and/or flags which are positioned for viewing through a window 208 in response to the configuration and condition of the dispenser 2. It is particularly desired to avoid any indication of retraction until substantially full retraction has been achieved. In the depicted embodiment, dispenser 2 includes a status window flag 186, shown best in FIGS. 2 and 10, pivotally mounted within a recessed region 188 of sliding body 100 to pivot about a pivot point 190. Flag 186 is bistable so that it remains in one of the two positions illustrated in FIG. 10. This is achieved using an S-shaped, over-center spring 192 having one end positioned in a cutout 194 formed in flag 186 adjacent pivot point 190 and another end positioned in a receptacle 196 formed in sliding body 100. Spring 192 is deflected between the solid line and dashed line positions of FIG. 10 through the engagement of a pair of trip pins 198 extending from a spring trip plate 200 carried by guide sleeve 8. Trip plate 200 is secured by guide sleeve 8 by the engagement of a pair of pins 202 which securely engage holes 204 formed in guide sleeve 8. Pins 198 pass through an opening 206 formed in guide sleeve 8. Trip pins 198 are positioned to lie on either side of spring 192. It would be possible to use projections (not shown) extending from the edges of opening 206 in place of the trip pins 198. When sliding body 100 is moved to the post-injection position of FIG. 9A, flag 186 is moved from the dashed line position to the solid line position of FIG. 10. Note, however, that this occurs only during the very end of travel of sliding body, for example, during the last 5 percent, preferably during the last 3 percent, more preferably the last one percent, of movement of the sliding body so that the user is assured that display of the flag 186 is a reliable indication of full retraction. Until the time substantially full retraction, flag 186 remains in the dashed line position of FIG. 10.

Figure 10:
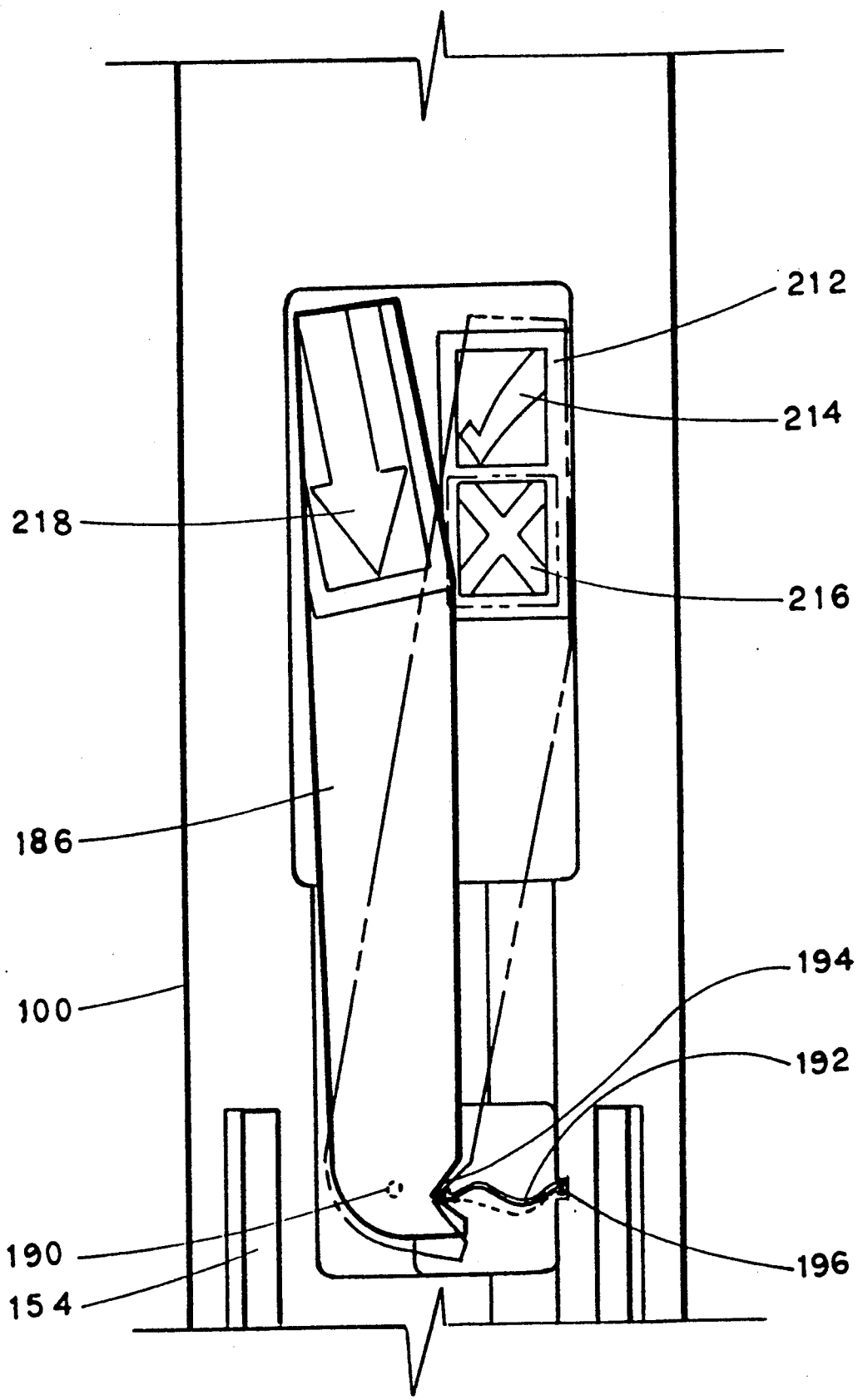
FIG. 10 is an enlarged simplified view of the slider body with the status window flag as it would be after the sliding body has moved distally to the post-injection position. At the end of the delivery stroke, the flag and over-center spring are shown in dashed lines to indicate their positions after the sliding body has been moved to the retracted position at the end of the return stroke.

Guide sleeve 8 has an offset status window 208 covered by a lens 210. Window 208 allows the user to view the position of flag 186. That is, when flag 186 is in the solid line position of FIG. 10 at the end of a delivery stroke, window 208 overlies a panel 212 formed in sliding body 100. As indicated in FIG. 10, panel 212 typically includes indicia 214, 216 which provide status information to the user. That is, when sliding body 100 is in the retracted position, window 208 overlies indicium 216. As sliding body 100 is moved distally, window 208 begins to pass over indicium 216 and onto indicium 214. However, because of the bistable nature of flag 186, the indicium 218, indicates that it is safe to perform the injection is seen through window 208 in the fully retracted position.

As the user pulls sliding body 100 away from guide sleeve 8, that is in proximal direction 170, status window 208 moves from overlying indicium 214 to overlying indicium 216. Only after sliding body 100 is in its fully retracted position will trip pins 198 contact spring 192 thus forcing the spring in such a way to cause status window flag 186 to move from its solid line to its dashed line position of FIG. 10. This also occurs during the last few percent of travel of sliding body 100. Only after the status flag 186 has been tripped will the indicium 218 be visible to the user. Preferably, indicium 218 is green while indicia 214, 216 are different colors from indicium 218 to quickly alert the user as to the status of pharmaceutical dispenser 2.

The display of the various indicia and the status flag is useful in assuring the user that the sliding body 100 has been fully retracted and the dispenser 2 is in condition for performing an injection. The indicia and status flag also provide additional advantages. As described more fully below, the status flag is useful in alerting the user that there is not sufficient pharmaceutical in one (or both) of the cartridges 32, 34 to deliver the dosage currently selected by the user, as described more fully below. Once a user has learned from the indicia and status flag that insufficient pharmaceutical remains, the indicia and status flag can also be used to provide a clear indication of how large a dosage can still be delivered with the remaining pharmaceutical, as described below.

The indicia and status flag are also useful in assisting the user to avoid waste of pharmaceutical. In one embodiment, this achieved by instructing the user to perform dose adjustment while the dispenser 2 is in the post-injection configuration (i.e., to avoid adjustment while the dispenser 2 is in the retracted position). If the user attempts to increase dosage after the retraction operation, there will be no undesirable effects and the apparatus will operate as intended. However, if the user attempts to decrease dosage after moving the sliding body to the fully retracted position, pharmaceutical will be expelled through the needle, causing waste. Therefore, by providing a clear indication of whether the dispenser 2 is in the retracted configuration, the user is assisted in avoiding a dosage change while the dispenser 2 is in the retracted position. A further aspect of the status flag 186 is the auditory "click" signal it produces when moving from one configuration to the other. This auditory signal is particularly useful for users with visual impairment. Thus, by providing an auditory "click" signal the above-described benefits of the indicia and status flag can be enjoyed by visually impaired users as well.

Lugs 152 are slidably positioned in slots 154 of slider body 100. As slider body 100 is translated forwardly (during an injection stroke), the surfaces of slider body 100 that define the base of slots 154 contact the bottom portions of lugs 152 and drive the lugs 152 and, thus, the ratchet disk housings 146 forwardly. Since stems 88 are coupled to ratchet disk housings 146 via ratchet discs 164, stems 88 and lugs 152 are driven forwardly the same distance. Once slider body 100 is in its post-injection position, as illustrated in FIG. 9A, the dose for subsequent injections can be adjusted. Specifically, dose screws 106 can be rotated to adjust the position of lugs 148 in slot 150 through the cooperation of threads 110 and 112. Although adjustment screw 106 can rotate relative to slider body 100, screws 106 cannot translate relative to the slider body. Accordingly, the position of lugs 148 in slots 150 determine the distance that ratchet disk housings 146 travel with sliding body 100 during retraction. For example, if dose screws 106 are rotated to position lugs 148 midway up slots 150, when slider body 100 is retracted, lugs 148 must move a distance corresponding to half the length of slots 150 before causing ratchet disk housing 146 to retract. In this way, the dose is set.

Referring to FIG. 2, dose adjustment screws 106 have four axially extending grooves 232 placed on equal quadrants of the screws. A pair of detent clips 234 are mounted within sliding body 100. Detent clips 234 engage grooves 232 as screws 106 are rotated to provide the user with both an tactile and an audible indication of the dose being chosen. The tactile and audible indications are particularly useful for vision-impaired users.

Housing body 162 of ratchet disk housing 146 has an inwardly extending projection 235, see FIG. 2, which rides along the end of dose grooves 92 formed in drive stems 88. When the contents 40, 42 of cartridges 32, 34 is insufficient to accommodate the selected dose, projection 235 will contact the end 222 of groove 92 to prevent any further proximal movement of sliding body 100. The user will know the contents of a cartridge is insufficient for the selected dose since the indicator flag will not be visible through the window 208. The user can, then, adjust dose knobs 114 to reduce the dose until sliding body 100 is in the fully retracted position. This will be indicated by movement of the indicator flag to align with the window 208. The user can then determine the available contents by viewing the position of dose indicator 132 after flag 186 has moved to the dashed line position of FIG. 10. Even after one cartridge is entirely depleted, pharmaceuticals can be dispensed from the non-depleted cartridge by selecting a "zero" dose for the depleted cartridge.

Figure 8:
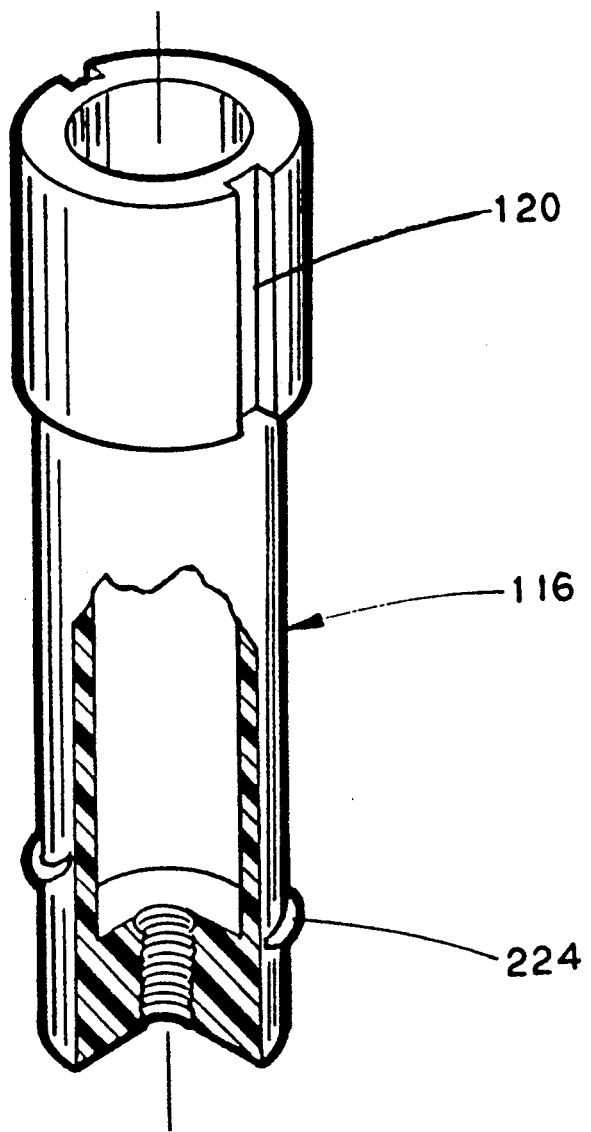
FIG. 8 is an enlarged view of a knob core of FIG. 2 showing the external release thread.

When it is decided to replace one or more of cartridges 32, 34, the user places sliding body 100 in the post-injection position of FIG. 9 shifts the cartridge release switch 236, and then, rotates dose knobs 114. This causes a single release thread, see FIG. 8, 224 formed on knob core 116 to engage an internal thread 226, see FIG. 7A, formed at the proximal end of sliding body 100 to advance. Release forks 228 (FIG. 5), in the distal direction 172 forcing the tapered tips 230 against fingers 166 of ratchet disks 164. This axial movement of release forks 228 causes housing 146 to move in the distal direction so that finger engaging taper tips 232 extending from cap 158 engage fingers 166 of anti-backup ratchet plate 82. Doing so causes fingers 166 to dilate thus releasing their grip on drive stem 88. The user can then remove manifold assembly 10 using release buttons 48, 50 to expose cartridges 32, 34. The cartridges can then be removed exposing drive stems 88. The drive stems can then be forced in the proximal direction, new cartridges can be mounted within receiving bores 28, 30 and a fresh manifold assembly mounted onto cartridge housing 6. In one embodiment, the new cartridges can be used to force the drive stems 88 in the proximal direction. In particular, by inserting new cartridges in the receiving boards 28, 30, and pushing the new cartridges down, either manually or by replacing the manifold 16, the pistons 96, 98 will engage the tops of the stems 88 and insertion of the cartridges will thus force the stems 88 proximally. Excessive movement of the stems 88 is avoided by contact of the proximal surface of the stems 88 with ledges 320 formed on the forks 228.

The fingers of both the ratchet plate 82 and ratchet disks 164 are configured so that they exert sufficient pressure against the stems 88 and are angled with respect to the stems 88 in such a manner that they can slide in a proximal direction with respect to the stems 88 but when moved in a distal direction will grasp the stems 88 and thus move the stems 88 along with the ratchet disks 164. In order to make sure the fingers retain this characteristic, it is necessary to assure that dilation of the fingers as described above is not so excessive that the fingers become bent or plastically deformed to the extent that, upon removal of the tapered tips 232, 230 the fingers will not relax to the desired configuration and angle. In order to avoid excessive dilation, as best seen in FIG. 5, housing body 162 and the coupled cap 158 are positioned normally (i.e., other than during dilation of the ratchet plate 82) spaced a distance 312 from the underside of the ledge 76. As described above, to dilate the fingers 166, the cap 158 is driven upward so that the tapered tips 232 contact the fingers 166. The amount by which the tapered tips 232 can be driven upward is limited by contact of the caps 158 with the bottom surface of the ledge 75 so that the cap 158 cannot be driven upward a distance greater than the spacing 312. This upper limit on the motion of the cap 158 provides an upper limit on the amount by which the fingers 166 of the ratchet plate 82 can be dilated. The underside 314 of the tapered tips 232 are tapered upward and spaced from the fingers 166 of the ratchet disk 164 to provide a stop preventing excessive dilation of the fingers 166 of the ratchet disk 164. Thus, the combination of the plate 76 acting as a stop to upward movement of the cap 158 and the tapered and spaced configuration of the lower surface 314 of the tapered tips 232 prevent excessive dilation of the fingers 166 of both the ratchet plate 82 and ratchet disks 164.

According to the depicted embodiment, the dispenser 2 is provided with a device to avoid accidental or premature release of the stem 88 and, preferably, to also prevent movement of the slider body 100 to the post-injection position while the stems 88 are released. According to the depicted embodiment, the release switch 236 projects proximally toward the knobs 114 and contacts the distal surface of the knobs to act as a hold-off. In particular, the bottom surface of the switch 236, when in the normal operating position, maintains the knobs 114 spaced a distance from the sliding body 100 sufficient to prevent engagement of the thread 224 with the internal thread 236. In this embodiment, in order to release the stems 88, the user grasps the head 185 of the switch 236 and pulls laterally outwardly so that the projection on the bottom of the switch 236 is positioned away from the knobs 114. The knobs 114 can then be moved distally a distance sufficient to engage thread 224 with thread 226, permitting release of the stems 88, as described above. In order to prevent movement of the sliding body 100, the switch 236 is provided with a periscope-shaped latch 238. When the switch 236 is pulled upward to the release position, the periscope latch 238 engages an opening 240 in the guide sleeve 8 (see FIG. 7), thus coupling the guide sleeve 8 to the sliding body 110 and preventing relative movement. After the desired movement of the stems 88, the knobs 114 are rotated to disengage a thread 224 from the thread 226 and lowered sufficiently to permit the release switch 236 to be pressed laterally inward, disengaging the periscope latch 238 (to, once again, permit relative movement of the sliding body 100 and guide sleeve 8) and positioning the projection on the bottom of the switch 236 adjacent the distal surfaces of the knobs 114, once again acting as a hold-off to prevent undesired release of the stems 88.

The indicia 214, 216 are useful in connection with a cartridge replacement by providing an indication to the user that the stems 88 have been released. When the stems are in the released configuration, the indicum 14 will be visible through the window 208. The user thus can refrain from attempting to change a cartridge until such time as the indicium 214 is visible.

Assuming pharmaceutical dispenser 2 is in the post-injection position of FIG. 9, the user selects the dose desired by rotating dose knobs 114. This causes dose indicator 132 to move along slot 138. The depicted configuration of the dose indicator system provides a number of advantages. By providing a linear scale with a moving indicator, dose indication is provided in a form that is intuitively legible to most users because of its analogous relationship to devices such as a bar graph or a speedometer or other "needle" type indicators with which many users will be already familiar. A moving indicator provides advantages over, e.g., the display of a number since the user is provided with not only a numeral indicator but also a positional indicator so that some redundancy of indication is provided. These aspects help safeguard against a mis-dose, particularly among visually impaired users. The dosage indicator of this embodiment is also useful in that it provides a type of memory since prior to adjustment it will indicate the dosage amounts used in the most recent injection. This is useful for persons who wish to select a dosage based on the most recent injection. It can also be useful for persons who followed a prescribed pattern of dosages but have difficulty remembering whether a particular injection from the pattern has been administered. Referring to the last previous dosage may assist such persons in determining which injection from a pattern of injections was last administered.

The position of dose indicator 132 is visible along the edges of guide sleeve 8 since guide sleeve 8 is made from a transparent material. However, the portion of guide sleeve 8 other than the rounded edges can be painted or otherwise made opaque, it is especially useful to render opaque that portion overlying recessed region 188 in sliding body 100 for providing visibility and contrasting indicia. At this point, indicator window 208 is over indicium 219 to tell the user that the sliding body is at the end of its delivery stroke. The user then presses on latch 84 and pulls sliding body 100 in the proximal direction to the retracted position. Once in that position, flag 186 trips and moves between its solid line position to its dashed line position of FIG. 10. Until the slider 100 reaches the retracted position, flag 186 is not visible beneath window 208. However, once in the retracted position, indicium 218 is visible showing the user that the next injection can be made. After the injection flag 186 returns to the solid line position of FIG. 10 and the procedure can be repeated.

With the exception of cartridges 32, 34, most of the components of dispenser 2 are made of injectable thermal plastic, such as polycarbonate. However, septum 24, diaphragm 18 and o-rings 140 are made of conventional elastomeric materials. Ratchet disks 164, ratchet plate 82 and over-center spring 192 are preferably made of spring quality stainless steel. Screw 78 and 118 are made of metal as well.

Modification and variation can be made to the disclosed embodiment without departing from the subject of the invention as defined in the following claims.

What is claimed is:

1. A fluid dispenser comprising:
   a housing;
   at least first and second variable volume containers mounted to the housing and including first and second exits and first and second movable elements by which the contents of the first and second containers can be forced through said first and second exits as the first and second movable elements are moved within said first and second containers respectively;
   a common exit fluidly coupled to the first and second exits;
   first and second drive stems drivingly coupled to the first and second movable elements, the first and second drive stems including axially extending drive surfaces; and
   a drive assembly, movable from a retracted position to a post-injection position for driving the first and second drive stems so to drive the first and second movable elements within said first and second containers in a cyclic manner, the drive assembly including:
   first and second drivers, including one-way drive elements, drivingly coupled to the first and second drive stems along the drive surfaces by the one-way drive elements; and first and second stroke adjusters for adjusting the relative distances the first and second drivers and the first and second drive stems associated therewith travel during each cycle of the driver so the amounts and proportions of the contents of the first and second containers forced through the first and second exists during each of one or more cycles of the drive assembly can be selected by the user while said amounts and proportions remain the same unless said relative distances are changed.

2. The dispenser of claim 1 further comprising means for indicating when the drive assembly is moved to the post-injection position.

3. The dispenser of claim 2 wherein the indicating means further comprises an indicator and means for actuating said indicator no earlier than during about the last 3% of the movement of the reciprocating drive assembly to the post-injection position.

4. The dispenser of claim 2 wherein the indicating means includes a visual indicator biased towards first and second stable positions corresponding to the post-injection and retracted positions respectively.

5. The dispenser of claim 2, wherein the indicating means includes an audible indication.

6. The dispenser of claim 4 wherein said visual indicator is spring-biased and is pivotally mounted to one of the housing and the drive assembly.

7. The dispenser of claim 6, wherein the visual indictor has a pivot point and is biased by an S-shaped spring positioned adjacent the pivot point.

8. The dispenser of claim 7, wherein the visual indicator is pivotally mounted to the drive assembly and the indicating means includes a pair of spring engaging elements carried by the housing and positioned to engage and deflect the S-shaped spring when the drive assembly is moved to the post-injection and the retracted positions.

9. The dispenser of claim 6, wherein the housing includes a status window, the visual indicator being visible through the status window when the drive assembly is in one of the post-injection and retracted positions, the visual indicator being not visible through the status window when the drive assembly reaches the other of the post-injection and retracted positions.

10. The dispenser of claim 1, further comprising latch means for automatically securing the drive assembly in the post-injection position until a user releases said latch means to help prevent inadvertent movement of the drive assembly from the post-injection position.

11. The dispenser of claim 1, further comprising means for selectively separating at least a portion of the housing and the variable volume containers therewith from the remainder of the dispenser to permit the user to change the variable volume containers.

12. The dispenser of claim 1, further comprising a manifold means, mounted to the housing, for fluidly coupling the first and second exits to a said common exit.

13. The dispenser of claim 12, wherein the manifold means includes means for selectively separating the manifold means from the housing so to permit the manifold means and the variable volume containers to be replaced by the user.

14. The dispenser of claim 1, wherein the variable volume containers include cartridges of the type including a needle-pierceable septum at one end, a movable piston and a pharmaceutical between the septum and the piston.

15. The dispenser of claim 1 wherein the drive surfaces of the drive stems are at least partially defined by axially extending slots formed in the drive stems.

16. The dispenser of claim 1 wherein the one-way drive elements include spring arms positioned at an acute angle to the drive surfaces, the spring arms engaging the drive surfaces.

17. The dispenser of claim 16 further comprising means for selectively releasing the one-way drive elements from the first and second drive stems, the selectively releasing means including a releasing fork mounted coaxially within the reciprocating drivers and adapted to selectively engage the spring arms so to deflect said spring arms away from the drive surfaces.

18. The dispenser of claim 17, further comprising means for locking said drive assembly to prevent movement toward said post-injection position when said drive elements are released.

19. The dispenser of claim 1 wherein the first and second stroke adjusters each include means for individually adjusting the amount each of said first and second drive stems moves during each cycle of the reciprocal drive assembly, each individual adjusting means including a dose control element by which a user selects said amounts of the contents of the respective first and second containers forced through the first and second exits.

20. The dispenser of claim 19, wherein each dose control element is an axially telescoping element to permit the user to easily rotatably manipulate one of said dose control elements without substantial interference with the other dose control element.

21. The dispenser of claim 20, wherein the first and second stroke adjusters each includes means for biasing the means for individually adjusting to a plurality of incremental adjustment positions.

22. The dispenser of claim 1 further comprising means for indicating the amounts of the contents of each of the first and second containers which are to be forced through the first and second exits during each of the one or more cycles of the reciprocating drive means.

23. The dispenser of claim 2, including means for transparently covering said indicating means.

24. The dispenser of claim 19 wherein the indicating means includes first and second visual displays.

25. The dispenser of claim 1 wherein the first and second reciprocating drivers includes:
first and second drive couplings mounted to and movable with the first and second stroke adjusters;
first and second one-way drive element housings, to which the one-way drive elements are mounted, axially slidably mounted to the housing;
the first and second drive couplings and the first and second one-way drive elements being drivingly coupled so that reciprocating movement of the first and second one-way drive elements causes movement of the one-way drive elements according to the adjustments of the first and second stroke adjusters.

26. The dispenser of claim 1 further comprising means for preventing the movement of the reciprocating drive assembly to the retracted position when the contents of at least one of the first and second containers available for discharge through the respective first and second exits is less than the amounts selected by the user using said first and second stroke adjusters.

27. The dispenser of claim 26, wherein the movement preventing means includes an axial groove formed along a portion of the length of each of the first and second drive stems.

28. The dispenser of claim 1, further comprising means for sensing when at least one of said drive stems has moved a predetermined amount and for preventing movement of said drive assembly to said retracted position in response to said sensing.

29. The dispenser of claim 28, wherein said predetermined amount is controlled by movement of said stroke adjusters.

30. A fluid dispenser comprising:
a housing;
at least a first variable volume container mounted to the housing and including a first exit and a first movable element by which the contents of the first container can be forced through said first exit as the first movable element is moved within said first variable volume container;
a drive stem drivingly coupled to the first movable element, the drive stem including an axially extending drive surface;
a drive assembly, movable between a post-injection position and a retracted position, for driving the drive stem so as to drive the first movable element within said first variable volume container in at least a first cycle, the drive assembly including:
a driver, including a one-way drive element, drivingly coupled to the drive stem along the drive surfaces by the one-way drive element; and
a stroke adjuster for adjusting the relative distance the driver and stem associated therewith travel during a cycle of the driver.

31. A dispenser, as claimed in claim 30, including an indicator coupled to said housing, movable between a first position, while said drive assembly is in said retracted position, and a second position in response to movement of said drive assembly substantially fully to said post-injection position.

32. A dispenser, as claimed in claim 31, wherein said indicator comprises a status flag pivotally mounted to the drive assembly at a pivot point.

33. A dispenser, as claimed in claim 32, further comprising a spring positioned adjacent the pivot point and oriented to bias the status flag to either of the post-injection and retracted positions.

34. A dispenser, as claimed in claim 33, further comprising a pair of spring engaging elements carried by the housing and positioned to engage and deflect the spring when the drive assembly is moved to the post-injection and the retracted positions.

35. A dispenser, as claimed in claim 32, further comprising a status window associated with the housing, the flag being visible through the status window when the drive assembly is in one of the post-injection and retracted positions, the flag being not visible through the status window when the drive assembly is in the other of the post-injection and retracted positions.

36. The dispenser of claim 30, further comprising a post-injection latch mounted to the housing and engagable with the drive assembly which, in response to moving the drive assembly to the post-injection position, secures the drive assembly in the post-injection position until a user releases said post-injection latch.

37. The dispenser of claim 30 further comprising at least a second variable volume container having a second exit and a common exit fluidly coupled to the first and second exits;

a manifold having at least a portion moveable to a first position to define a fluid path from the first and second exits to a said common exit.

38. The dispenser of claim 37, wherein the manifold includes a latch movable from a first position holding the manifold to the housing to a second position allowing the manifold to separate from the housing.

39. The dispenser of claim 30, further comprising a stop surface formed in said drive stem positioned to engage said drive assembly to prevent movement thereof when said drive assembly has driven said stem a predetermined amount so that the stroke determined by said stroke adjusters exceeds the effective remaining length of said variable volume container.

40. A fluid dispenser comprising:
a housing;
first and second pharmaceutical-containing cartridges mounted within the housing, the cartridges each including a movable piston, an exit end and a fluid between the piston and the exit end;
a common exit fluidly coupling the exit ends of the cartridges; and
a reciprocating drive assembly comprising:
first and second drive stems adapted to engage the pistons of the first and second cartridges to drive the contents of the cartridges through the exit ends and to the common exit;
a sliding body slidably mounted to the housing for movement in delivery and return directions between post-injection and retracted positions said positions defining an injection stroke length;
first and second reciprocating drivers, coupled to the sliding body, including one-way drive elements coupled to the first and second drive stems, the one-way drive elements and the first and second drive stems configured so that the first and second reciprocating drivers move the first and second drive stems only towards the first and second cartridges during the movement of the sliding body; and
means for separately adjusting the distances the first and second reciprocating drivers move the first and second drive stems towards the first and second cartridges during the movement of the sliding body in the delivery direction so the amounts and proportions of the contents of the first and second cartridges forced through the first and second exit ends and to the common exit during each of one or more cycles of the reciprocating drive assembly can be selected by the user while said amounts and proportions remain the same unless said separately adjusting means are changed.

41. A fluid dispenser comprising:
a housing;
first and second pharmaceutical-containing cartridges mounted within the housing, the cartridges each including a movable piston, an exit end and a fluid between the piston and the exit end;
a common exit fluidly coupling the exit ends of the cartridges; and
a reciprocating drive assembly comprising:
first and second drive stems adapted to engage the pistons of the first and second cartridges to drive the contents of the cartridges through the exit ends to common exit;
a sliding body slidably mounted to the housing for movement in delivery and return directions between post-injection and retracted positions, said positions defining an injection stroke length;

first and second reciprocating drivers, coupled to the sliding body, including one-way drive elements coupled to the first and second drive stems, the one-way drive elements and the first and second drive stems configured so that the first and second reciprocating drivers move the first and second drive stems only towards the first and second cartridges during the movement of the sliding body; and a user-adjustable coupler for coupling said reciprocating drivers in any of a plurality of positions with respect to said sliding body, said coupler including coupling means for permitting movement of said sliding body a first distance without corresponding movement of said first reciprocating driver and for forcing corresponding movement of said first reciprocating driver when said sliding body is moved beyond said first distance, while said first reciprocating driver is coupled in a first position, and said coupler including means for permitting movement of said sliding body a second distance, different from said first distance, without corresponding movement of said second reciprocating driver and for forcing corresponding movement of said second reciprocating driver when said sliding body is moved beyond said second distance while said second reciprocating driver is coupled in a second position.

42. A pharmaceutical dispenser comprising:

a housing;

first and second variable volume containers mounted to the housing and including first and second exits and first and second movable elements by which the contents of the first and second containers can be forced through said first and second exits as the first and second movable elements are moved from first and second staring positions towards first and second ending positions;

a manifold having an interior, a common exit fluidly coupled to the interior and the first and second exits, and a resilient wall partially bounding said interior, said interior wall being deflectable to an extended position by an elevated fluid pressure within said interior which tends to expel the fluid through said common exit to reduce the amount of the fluid therein;

first and second drive stems drivingly coupled to the first and second movable elements; and a reciprocating drive assembly for reciprocatingly drivingly the first and second drive stems so as to drive the first and second movable elements from the first and second starting positions towards the first and second ending positions by amounts which are user-selectable and independent.

43. A pharmaceutical dispenser, as claimed in claim 42, wherein said manifold includes a check valve for preventing fluid flow in a direction into one of said variable volume containers.

* * * * *